United States Patent [19]
Ligon et al.

[11] Patent Number: 5,756,087
[45] Date of Patent: May 26, 1998

[54] GENETICALLY MODIFIED PSEUDOMONAS STRAINS WITH ENHANCED BIOCONTROL ACTIVITY

[75] Inventors: James M. Ligon, Apex; Dwight S. Hill, Cary; Stephen T. Lam, Raleigh; Thomas D. Gaffney, Chapel Hill; Nancy Torkewitz, Hurdle Mills, all of N.C.

[73] Assignee: Novartis Finance Corporation, New York, N.Y.

[21] Appl. No.: 761,258

[22] Filed: Dec. 6, 1996

[51] Int. Cl.⁶ .................... A01N 63/00; C12N 1/21; C05F 11/08
[52] U.S. Cl. .................... 424/93.2; 71/6; 424/93.47; 424/405; 435/252.34; 435/876; 504/111; 504/117
[58] Field of Search ............... 435/252.34; 424/93.2, 424/93.47, 405; 71/6; 504/101, 117

[56] References Cited

U.S. PATENT DOCUMENTS 5,348,742  9/1994  Howell et al. .................... 424/93.47
5,496,547  3/1996  Lam et al. ........................ 424/93.47

FOREIGN PATENT DOCUMENTS

| 472494 | 2/1992 | European Pat. Off. |
| WO94/01561 | 1/1994 | WIPO |
| WO95/33818 | 12/1995 | WIPO |

*Primary Examiner*—George C. Elliott
*Assistant Examiner*—Johnny F. Railey, II
*Attorney, Agent, or Firm*—J. Timothy Meigs

[57] ABSTRACT

Strains of Pseudomonas have been genetically engineered to have enhanced biocontrol properties. The strains of the invention are particularly effective against plant pathogenic fungi such as species of Rhizoctonia and Pythium, because the strains produce enhanced amounts of antifungal metabolites such as pyrrolnitrin that are active against these fungal pathogens. Both the genetically modified biocontrol strains and the antifungal metabolites can be used as active agents for biocontrol compositions.

21 Claims, 5 Drawing Sheets tac Promoter/rrnB Terminator Fragment

BssHII (1) BglII (7)
GCGCGCAGATCTGGGCTTATCGACTGCACGGTGCACCAATGCTTCTGG
CGTCAGGCAGCCATCGGAAGCTGTGGTATGGCTGTGCAGGTCGTAAAT
CACTGCATAATTCGTGTCGCTCAAGGCGCACTCCCGTTCTGGATAATG
TTTTTGCGCCGACATCATAACGGTTCTGGCAAATATTCTGAAATGAG

HincII (195)
CTGTTGACAATTAATCATCGGCTCGTATAATGTGTGGAATTGTGAGCG

SmaI (270)        SalI (281)
                       EcoRI (265)    BamHI (275)       PstI (287)
GATAACAATTTCACACAGGAAACAGAATTCCCGGGGATCCGTCGACCT

XbaI (293)XhoI (299)KpnI (305)NotI (311)   HindIII (319)
GCAGTCTAGACTCGAGGGTACCGCGGCCGCAAGCTTGGCTGTTTTGGC

GGATGAGAGAAGATTTTCAGCCTGATACAGATTAAATCAGAACGCAGA

AGCGGTCTGATAAAACAGAATTTGCCTGGCGGCAGTAGCGCGGTGGTC

CCACCTGACCCCATGCCGAACTCAGAAGTGAAACGCCGTAGCGCCGAT

GGTAGTGTGGGGTCTCCCCATGCGAGAGTAGGGAACTGCCAGGCATCA

AATAAAACGAAAGGCTCAGTCGAAAGACTGGGCCTTTCGTTTTATCTG

TTGTTTGTCGGTGAACGCTCTCCTGAGTAGGACAAATCCGCCGGGAGC

GGATTTGAACGTTGCGAAGCAACGGCCCGGAGGGTGGCGGGCAGGACG

CCCGCCATAAACTGCCAGGCATCAAATTAAGCAGAAGGCCATCCTGAC

GGATGGCCTTTTGCGTTTCTACAAACTCTTTTGTTTATTTTTCTAAA

TACATTCAAATATGTATCCGCTCATGAGACAATAACCCTGATAAATGC
TTCAATAATATTGAAAAAGGAAGAGTATGAGTATTCAACATTTCCGTG
TCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTG
CACGAGTGGGTTACATCGAACTGGATCTCAACAGCGGTAAGATCCTTG
AGAGTTTTCGCCCCGAAGAACGTTTTCCAATGATGAGCACTTTTAAAG

BssHII (1092)
                           BglII (1086)
TTCTGCTATGTGGCGCGGTATTATCCCGTAGATCTGCGCGC

GENETICALLY MODIFIED PSEUDOMONAS STRAINS WITH ENHANCED BIOCONTROL ACTIVITY

FIELD OF THE INVENTION

The present invention relates to genetically modified strains of Pseudomonas that have improved biocontrol properties. More specifically it relates to strains that are effective against plant pathogenic fungi.

BACKGROUND OF THE INVENTION

It has been recognized that crops grown in some soils are naturally resistant to certain fungal pathogens. Furthermore, soils that are conducive to the development of these diseases can be rendered suppressive or resistant to the pathogen by the addition of small quantities of soil from a suppressive field (Scher and Baker (1980) Phytopathology 70: 412–417). Conversely, suppressive soils can be made conducive to fungal disease susceptibility by autoclaving, indicating that the factors responsible for disease control are biological. Subsequent research has demonstrated that root colonizing bacteria are responsible for this phenomenon, which is known as biological disease control (Cook and Baker (1983), The Nature and Practice of Biological Control of Plant Pathogens; Amer. Phytopathol. Soc., St. Paul, Minn.).

In many cases, the most efficient strains of biological disease controlling bacteria are fluorescent pseudomonads (Weller et al. (1983) Phytopathology, 73: 463–469). These bacteria have also been shown to promote plant growth in the absence of a specific fungal pathogen by the suppression of detrimental rhizosphere microflora present in most soils (Kloepper et al. (1981) Phytopathology 71: 1020–1024). Important plant pathogens that have been effectively controlled by seed inoculation with these bacteria include *Gaemannomyces graminis*, the causative agent of take-all in wheat (Cook et al.(1976) Soil Biol. Biochem 8: 269–273) and Pythium and Rhizoctonia, pathogens that cause damping off of cotton (Howell et al. (1979) Phytopathology 69: 480–482). Rhizoctonia is a particularly problematic plant pathogen for several reasons. First, it is capable of infecting a wide range of crop plants, and second, there are no commercially available chemical fungicides that are effective in controlling the fungus.

Many biological disease controlling Pseudomonas strains produce antibiotics that inhibit the growth of fungal pathogens (Howell et al. (1979) Phytopathology 69:480–482; Howell et al. (1980) Phytopathology 70: 712–715). These antibiotics have been implicated in the control of fungal pathogens in the rhizosphere. For example, Howell et al. (Phytopathology 69: 480–482; 1979) disclose a strain of *Pseudomonas fluorescens* that produces an antibiotic substance antagonistic to *Rhizoctonia solani*. In addition, other strains of *Pseudomonas fluorescens* having enhanced biocontrol activity against plant pathogenic fungi such as Rhizoctonia and Pythium are disclosed in U.S. Pat. Nos. 5,348,742 and 5,496,547, both of which are hereby incorporated by reference in their entireties. Several other past studies have focused on the effects of mutations that result in the inability of the disease control bacterium to synthesize these antibiotics (Kloepper et al. (1981) Phytopathology 71: 1020–1024; Howell et al. (1983) Can. J. Microbiol. 29: 321–324). In these cases, the ability of the organism to control the pathogen is reduced, but not eliminated.

A particularly effective antibiotic against fungal pathogens is pyrrolnitrin, which is biosynthesized from tryptophan (Chang et al. J. Antibiot. 34: 555–566). Pyrrolnitrin is a phenylpyrrole derivative with strong antibiotic activity that has been shown to inhibit a broad range of fungi (Homma et al., Soil Biol. Biochem. 21: 723–728 (1989); Nishida et al., J. Antibiot., ser. A, 18: 211–219 (1965)). Pyrrolnitrin was originally isolated from *Pseudomonas pyrrocinia* (Arima et al., J. Antibiot., ser. A, 18: 201–204 (1965)), but has since been isolated from Myxococcus species, Burkholdaria species, and several other Pseudomonas species such as *Ps. fluorescens* (Gerth et al. J. Antibiot. 35: 1101–1103 (1982); J. N. Roitman, N. E. Mahoney and W. J. Janisiewicz, Applied Microbiology and Biotechnology 34:381–386 (1990)). The compound has been reported to inhibit fungal respiratory electron transport (Tripathi & Gottlieb, J. Bacteriol. 100: 310–318 (1969)) and uncouple oxidative phosphorylation (Lambowitz & Slayman, J. Bacteriol. 112: 1020–1022 (1972)). It has also been proposed that pyrrolnitrin causes generalized lipoprotein membrane damage (Nose & Arima, J. Antibiot., ser A, 22: 135–143 (1969); Carlone & Scannerini, Mycopahtologia et Mycologia Applicata 53: 111–123 (1974)). U.S. patent application Ser. No. 08/729,214, and U.S. Pat. No. 5,639,949, both of which are hereby incorporated by reference in their entireties, describe the cloning and characterization of the pyrrolnitrin biosynthetic genes from *Ps. fluorescens* and *Ps. pyrrocinia*.

An important factor in biological control is the ability of a biocontrol organism to compete in a given environment (Baker et al. (1982) Biological Control of Plant Pathogens, American Phytopathological Society, St. Paul, Minn., pages 61–106). Thus, it is desirable to obtain strains of biocontrol agents that effectively control the growth of fungal pathogens such as Rhizoctonia and Pythium and that are also able to aggressively compete with indigenous bacteria and microflora existing in the rhizosphere of the plant.

SUMMARY OF THE INVENTION

The present invention is drawn to genetically engineered biocontrol strains of Pseudomonas that are able to effectively control pathogenic attack on crop plants. Preferred biocontrol strains include the following strains of *Pseudomonas fluorescens*, which are described in detail in the Experimental section below: CGA376146, CGA364473, CGA375258, CGA376148, CGA364476, CGA375260, CGA375259, CGA378584, and CGA267pPhz. The biocontrol strains of the invention produce at least one antifungal substance that is capable of inhibiting a broad spectrum of plant pathogens such as Rhizoctonia and Pythium. In a preferred embodiment, the biocontrol strains of the invention produce enhanced quantities of pyrrolnitrin. Such strains have increased biocontrol properties and are able to aggressively compete in the plant rhizosphere. The present invention is also drawn to biocontrol compositions comprising the biocontrol strains of the invention in combination with a chemical fungicide such as a metalaxyl compound. In addition, methods of making the biocontrol strains as well as methods of using the strains and biocontrol compositions for control of pathogenic attack on crops are described.

BRIEF DESCRIPTION OF THE FIGURES

FIG. 3 (SEQ ID No:7) shows the nucleotide sequence of the tac promoter/rrnB transcription terminator cassette derived from plasmid pKK223-3. The tac promoter and rrnB transcription terminator are indicated below the sequence by thick and thin arrows, respectively. The position of important restriction sites is indicated above the sequence.

BRIEF DESCRIPTION OF THE SEQUENCES IN THE SEQUENCE LISTING

Figure 1:
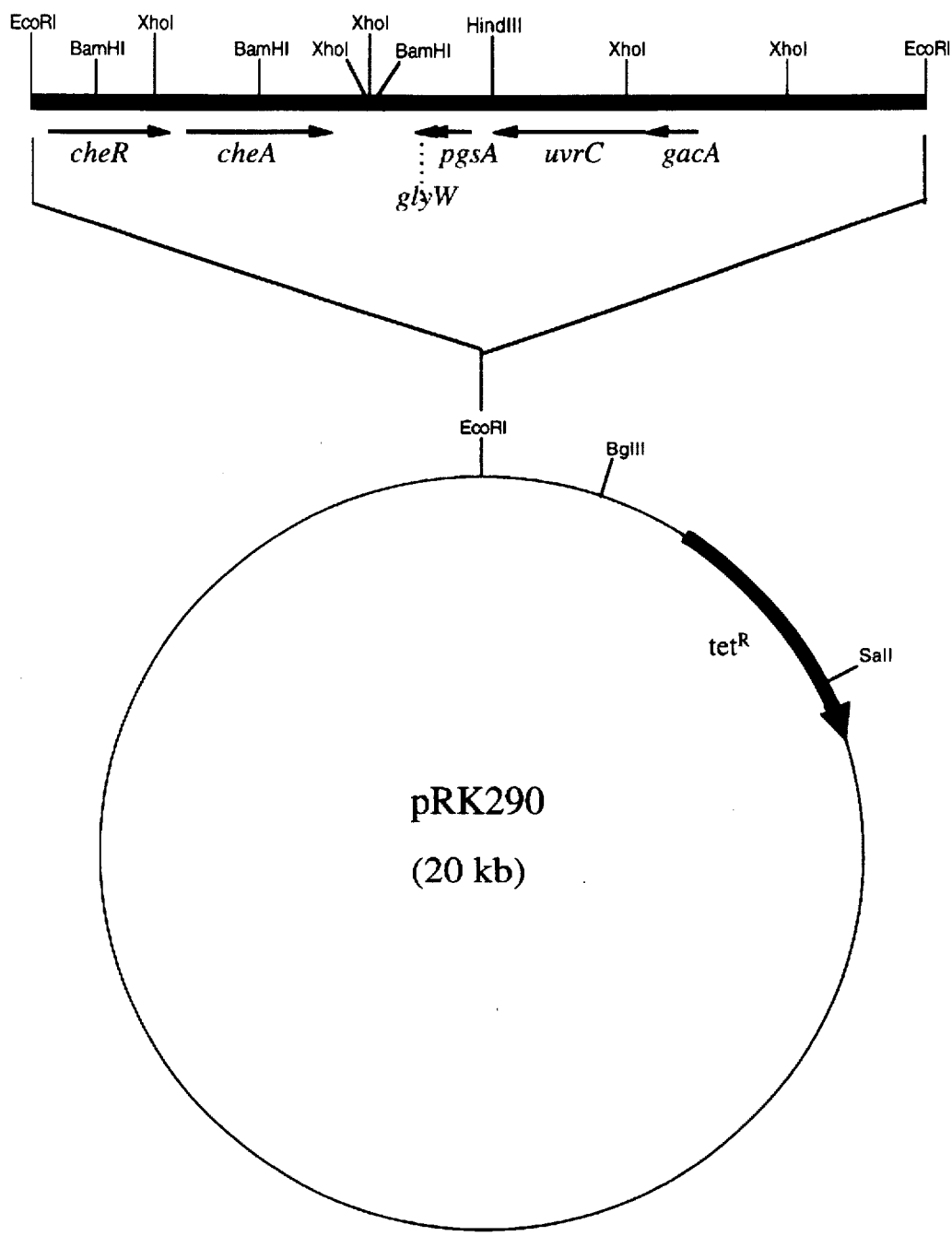
FIG. 1 is a plasmid map of plasmid PE11. The 11 kb EcoRI fragment (shaded box) containing the gacA gene derived from *P. fluorescens* strain CGA267356 is shown in expanded view cloned into the EcoRI site of plasmid pRK290. The positions of the genetic elements within this fragment are indicated by arrows below the map.

SEQ ID NO:1 is the nucleotide sequence of the 11 kb EcoRI fragment containing the gacA gene and derived from the chromosome of *Pseudomonas fluorescens* strain CGA267356. The coding sequences in this sequence include genes encoding: a methyltransferase (bases 210–1688) with homology to the cheR and frzF genes from *E. coli* and *Myxococcus xanthus*, respectively; a sensor kinase (bases 1906–3633) with homology to the rcsC, frzE and bvgS genes of *E. coli*, *M. xanthus*, and *Borditella pertussis*, respectively; a tRNA (bases 4616–4691, complementary DNA strand) with homology to glyW from *E. coli*; CDP-diacylglycerol-glycerol-3-phosphate-3-phosphatidyltransferese (bases 4731–5318, complementary DNA strand) with homology to pgsA; UVR exonuclease subunit C (bases 5574–7397, complementary DNA strand) with homology to uvrC; and a response regulator/transcription activator (gacA; bases 7400–8041, complementary DNA strand) with homology to the uvrY and gacA genes of *E. coli* and *P. fluorescens*, respectively.

SEQ ID NO:2 is the nucleotide sequence of the native gacA regulatory gene.

SEQ ID NO:3 is the protein sequence encoded by the native gacA regulatory gene.

SEQ ID NO:4 is the nucleotide sequence of the ATG/gacA regulatory gene, wherein the first base in the coding sequence has been changed from the native thymidine (T) to an adenine (A) to create the more efficient ATG translation initiation codon.

SEQ ID NO:5 is the protein sequence encoded by the altered ATG/gacA regulatory gene.

SEQ ID NO:6 is the nucleotide sequence of the pyrrolnitrin gene cluster.

SEQ ID NO:7 is the nucleotide sequence of the tac promoter/rrnB transcription terminator cassette.

SEQ ID NO:8 is the nucleotide sequence of the lemA gene.

SEQ ID NO:9 is the nucleotide sequence of the gac*A regulatory gene, wherein the adenine (A) base at position 395 has been changed from the native adenine (A) to a guanine (G) so that codon 132 encodes an arginine residue instead of the usual glutamine.

SEQ ID NO: 10 is the protein sequence encoded by the altered gac*A regulatory gene.

SEQ ID NO: 11 is the nucleotide sequence of the phenazine gene cluster.

DETAILED DESCRIPTION OF THE INVENTION

The present invention provides improved biocontrol strains of Pseudomnonas that can be used to control pathogenic attack on crop plants. Such strains are able to aggressively compete in the plant rhizosphere as well as produce one or more antifungal substances that are effective against a broad spectrum of plant pathogenic fungi such as Rhizoctonia and Pythium.

The biocontrol strains of the present invention are important for several reasons. First, Rhizoctonia such as *Rhizoctonia solani* are particularly pernicious plant pathogens. The affected plants include beans, wheat, tomato and potato, in addition to cotton. Second, there are few environmentally safe and effective fungicide treatments available for the protection of crops from Rhizoctonia. Therefore, the use of the disclosed biocontrol strains to control or prevent Rhizoctonia infections in crop plants provides an environmentally safe and effective method of controlling this and other plant pathogens.

*Pseudomonas fluorescens* strain CGA267356 (also known as both MOCG134 and BL915) has been shown to be effective in controlling plant pathogenic fungi such as Rhizoctonia and Pythium. Strain CGA267356 is one of the subjects of U.S. Pat. No. 5,348,742. Two mutants of CGA267356, strains CGA321730 (a.k.a. MOCG134-8392) and CGA319115, have been constructed and shown to demonstrate even better biological control (biocontrol) of these phytopathogens. CGA321730 and CGA319115 are the subject of U.S. Pat. No. 5,496,547.

Two genes have been isolated from strain CGA267356 that encode proteins that regulate the synthesis of several antifungal compounds produced by the strain, including the antifungal metabolite pyrrolnitrin (pm). These are the lemA gene and gafA (a.k.a. gacA) gene that encode sensor kinase and response regulator proteins, respectively, which function as a typical two-component bacterial regulatory system. These genes and their use to activate biocontrol activity in biocontrol strains are described in U.S. Pat. No. 5,670,350, which is hereby incorporated by reference in its entirety. In addition, U.S. Pat. No. 5,639,949 and U.S patent application Ser. No. 08/729,214 describe a four gene cluster isolated from strain CGA267356 that encodes proteins that direct the biosynthesis of pyrrolnitrin.

In the present invention, the lemA and gacA regulatory genes and the pyrrolnitrin biosynthetic genes have been utilized to genetically modify parent *Ps. fluorescens* strain CGA267356 to construct altered strains that demonstrate enhanced production of antifungal metabolites, i.e. pyrrolnitrin, and accordingly enhanced biocontrol activity. In addition, genes from *Pseudomonas aureofaciens* strain 30-84 that are involved in the synthesis of the antifungal metabolite phenazine-1-carboxylic acid (PCA) have been utilized to genetically modify parent *Ps. fluorescens* strain CGA267356 to produce PCA, thereby improving the biocontrol activity of strain CGA267356.

A further embodiment of the invention provides a method for controlling or inhibiting the growth of a plant pathogenic fungus by applying the genetically engineered biocontrol strains of the invention to an environment in which the plant pathogenic fungus may grow. This can be to the plant/s or parts of the plant/s or seeds (prior to planting) of the plant/s to be protected, or alternatively to soil in which the plant/s to be protected are growing or will grow. The biocontrol strains are applied in an effective amount; that is, in an amount sufficient to control or inhibit the pathogen. The rate of application may vary according to the crop to be protected, the efficacy of the biocontrol strain, the pathogen to be controlled, and the severity of the disease pressure. Generally, the rate of application is about $1.3 \times 10^5$ cfu/cm to about $1.3 \times 10^{10}$ cfu/cm, specifically about $1.3 \times 10^6$ cfu/cm to about $1.3 \times 10^9$ cfu/cm, more specifically about $1.3 \times 10^7$ cfu/cm to about $1.3 \times 10^8$ cfu/cm.

A more particular embodiment of the present invention provides methods of inhibiting the growth of Rhizoctonia and Pythium by applying the biocontrol strains of the invention to environments in which the plant pathogenic fungi may grow. This can be to the plant/s or parts of the plant/s or seeds (prior to planting) of the plant/s to be protected, or alternatively to soil in which the plant/s to be protected are growing or will grow. As noted above, the rate of application varies depending on various factors. However, the general rate of application is about $1.3 \times 10^5$ cfu/cm to about $5 \times 10^9$ cfu/cm, specifically about $1.3 \times 10^6$ cfu/cm to about $1.3 \times 10^9$ cfu/cm more specifically about $1.3 \times 10^7$ cfu/cm to about $1.3 \times 10^8$ cfu/cm.

The recombinant biocontrol strains of the present invention may be used in any manner known in the art, including coating seeds with an effective amount of the biocontrol strains, in furrow application of the biocontrol strains directly into the soil, and in foliar application. Such methods are well known in the art and are described, for example, in U.S. Pat. No. 5,348,742 and in the published European Application EP 0 472 494 A2, which is hereby incorporated by reference. Furthermore, the strains of this application can also be mixed in formulation with known pesticides in a manner described in WO 94/10845, which disclosure is herein incorporated by reference.

The following Examples are offered by way of illustration and not by way of limitation.

EXPERIMENTAL

EXAMPLE 1

Construction of *Pseudomonas fluorescens* Strain CGA376146 (8392 pE11)

Strain CGA376146 was constructed by introducing plasmid pE11 into *P. fluorescens* strain CGA321730 (MOCG-0134-8392) by conjugation. Strain CGA321730 is described in U.S. Pat. No. 5,496,547 and is a transposon mutant of wild-type *P. fluorescens* strain CGA267356 (U.S. Pat. No. 5,348,742) that has enhanced biocontrol activity over the wild-type strain. Strain CGA267356 has been deposited with the ATCC and assigned ATCC accession number 55169. Strain CGA321730 has been deposited with the NRRL and assigned accession number NRRL B-21173. Plasmid pE11 (FIG. 1) was constructed by ligating the 11 kilobase (kb) EcoRI fragment derived from the chromosome of strain CGA267356 into the broad host range plasmid vector pRK290 (Ditta et al., *Proc. Natl. Acad. Sci. USA* 77:7347–7351 (1980). Plasmid pE11 has been deposited with ATCC and has been assigned ATCC accession number 40869.

The 11-kb EcoRI fragment contains the gacA (gafA) gene that encodes a response regulator protein known to regulate the synthesis of antifungal compounds. This 11-kb EcoRI fragment is described in U.S. Pat. No. 5,670,350 and is set forth herein as SEQ ID NO:1. The plasmid vector, pRK290, used in constructing pE11, is derived from native Pseudomonas plasmids. It is mobilizable but not self-transmissible by conjugation and it carries a tetracycline resistance gene (Ditta et al., 1980).

New strain CGA376146 has been shown to produce higher amounts of the antifungal metabolite pyrrolnitrin (Table 1) and to have higher biocontrol activity (Table 2) compared to the related strains CGA267356 and CGA321730.

EXAMPLE 2

Construction of *Pseudomonas fluorescens* Strain CGA364473 (ATG/gac)

*P. fluorescens* strain CGA364473 was derived from parent *P. fluorescens* strain CGA267356 by changing a single base in the chromosome of the parent strain.

The native gacA regulatory gene begins with the unusual TTG translation initiation codon (SEQ ID NO:2). All proteins in nature are synthesized with methionine as the first amino acid on the amino terminus and ATG is the only codon that encodes methionine. Therefore, the normal translation initiation codon for most genes is ATG. Alternate translation initiation codons GTG and TTG will also result in the incorporation of methionine as the first amino acid since methionine must always be the first amino acid in a newly synthesized protein, but they usually cause a reduction in the efficiency of translation. As a result, fewer protein molecules are made from the same amount of messenger RNA.

To create strain CGA364473, the first base in the coding sequence of the gacA gene was changed from a thymidine (T) to an adenine (A) to create the more efficient ATG translation initiation codon (SEQ ID NO:4). This change was created in vitro by PCR technology and the native gacA gene in the chromosome of strain CGA267356 was replaced with the ATG/gacA gene by homologous gene replacement. The amino acid sequence of the GacA protein encoded by this altered gacA gene (SEQ ID NO:5) is identical to that encoded by the native gene (SEQ ID NO:3), but translation should be more efficient, resulting in synthesis of higher amounts of the protein.

New strain CGA364473 has been shown to produce higher amounts of the antifungal metabolite pyrrolnitrin (Table 1) and to have higher biocontrol activity (Table 2) compared to strain CGA267356.

EXAMPLE 3

Construction of *Pseudomonas fluorescens* Strain CGA375258 (pPrn)

Figure 2:
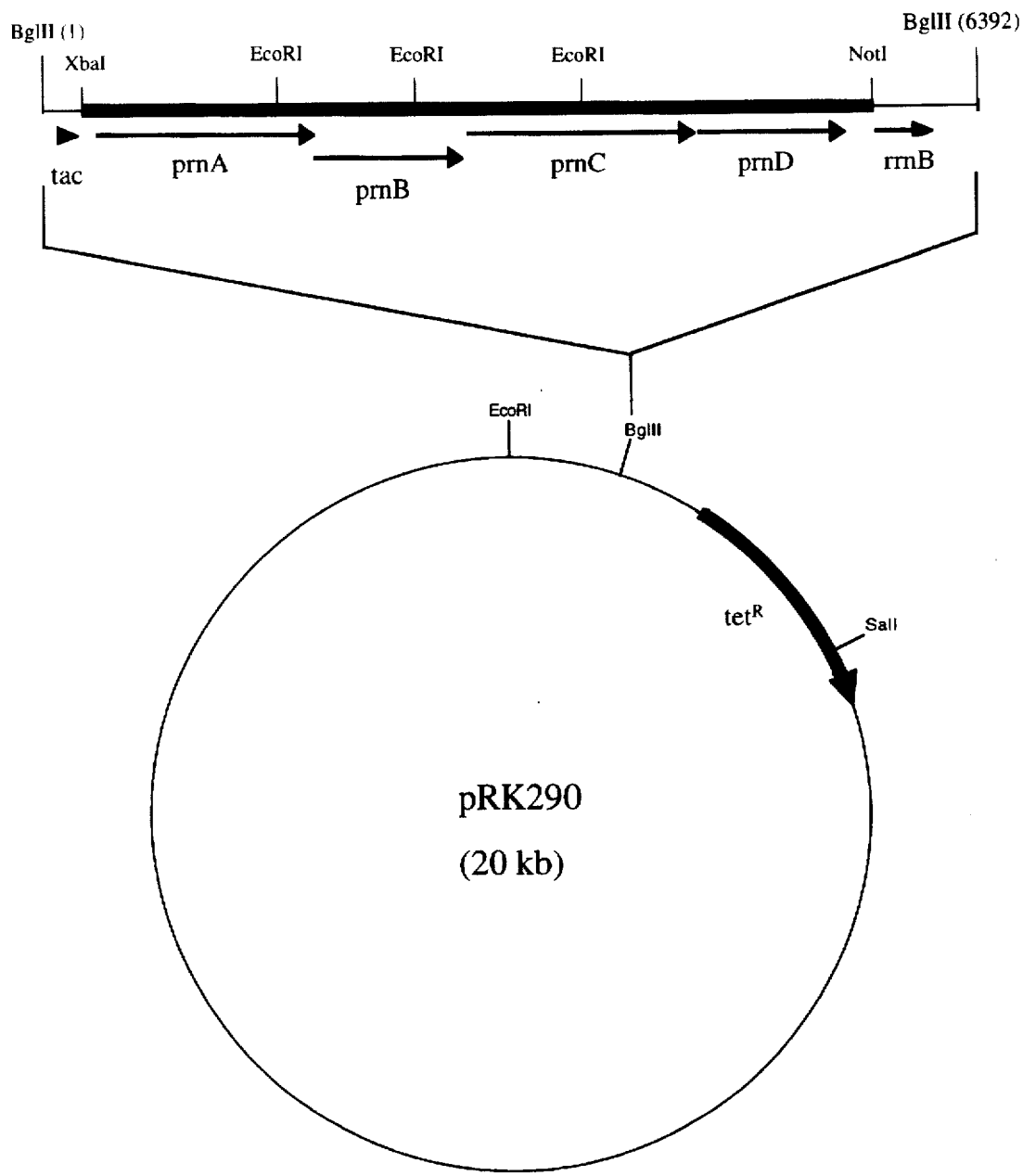
FIG. 2 is a plasmid map of plasmid pPrn. The 6.9 kb BglII fragment (heavy line) containing the tac promoter and rrnB transcription terminator derived from plasmid pKK223-3 and the prnABCD gene cluster (shaded box) derived from *P. fluorescens* strain CGA267356 are shown in expanded view cloned into the BglII site of plasmid pRK290. The positions of the genetic elements within this fragment are indicated by arrows below the map.

Strain CGA375258 was created by introducing plasmid pPrn into the parent *P. fluorescens* strain CGA267356. Plasmid pPrn was constructed by cloning a 6.2 kb XbaI/NotI gene fragment from plasmid pCIB 169 (which was derived from *P. fluorescens* strain CGA267356) into the expression vector pKK223-3, as described in Examples 7–11 of U.S. Pat. No. 5,639,949 and U.S. Ser. No. 08/729,214. (See SEQ ID NO:6). Plasmid pCIB 169 has been deposited with the NRRL and assigned accession number NRRL B-21256. The 6.2 kb XbaI/NotI gene fragment of SEQ ID NO:6 contains the prnABCD gene cluster that encodes genes for the biosynthesis of pyrrolnitrin as described in Ser. Nos. 08/258, 261 and 08/729,214. A 6.9 BglII fragment containing the prnABCD gene cluster with the tac promoter (see SEQ ID NO:7) upstream of the gene cluster and the rrnB transcription terminator (SEQ ID NO:7) downstream of the cluster was subsequently cloned into the BglII site of plasmid pRK290 to create plasmid pPrn (FIG. 2).

The tac promoter is a small DNA fragment (less than 100 bases) derived from *E. coli*, which is known to be a regulatory element or promoter (Amann, et al, Gene 25:167–178 (1983)) that does not itself encode a protein product. SEQ ID NO:7 presents the sequence of the BssHII DNA fragment containing the tac promoter and the rrnB transcription terminator derived from plasmid pKK223-3. The tac promoter is known to be highly expressed in a constitutive manner in Pseudomonas. Its use with the prn genes causes constitutive, high-level expression of these genes. On the other hand, in the native strain, the promoter for the pyrrolnitrin genes is regulated by the gacA gene product; accordingly, the pyrrolnitrin genes are expressed in the native strain only in the stationary phase of growth.

New strain CGA375258 has been shown to produce higher amounts of the antifungal metabolite pyrrolnitrin (Table 1) and to have higher biocontrol activity (Table 2) compared to the related strain CGA267356.

EXAMPLE 4

Construction of *Pseudomonas fluorescens* Strain CGA376148 (8392 pPrn)

The chromosomal background of strain CGA376148 is the same as strain CGA376146 (Example 1). In addition, strain CGA376148 contains the plasmid pPrn (Example 3) that carries the tac promoter fused to the prnABCD gene cluster.

New strain CGA376148 has been shown to produce higher amounts of the antifungal metabolite pyrrolnitrin (Table 1) and to have higher biocontrol activity (Table 2) compared to the related strain CGA267356.

EXAMPLE 5

Construction of *Pseudomonas fluorescens* Strain CGA364476 (pLem/Gac)

Strain CGA364476 is the same as wild-type strain CGA267356, except that strain CGA364476 also contains a plasmid with the lemA and gacA genes derived from the chromosome of the wild-type strain CGA267356.

Figure 4:
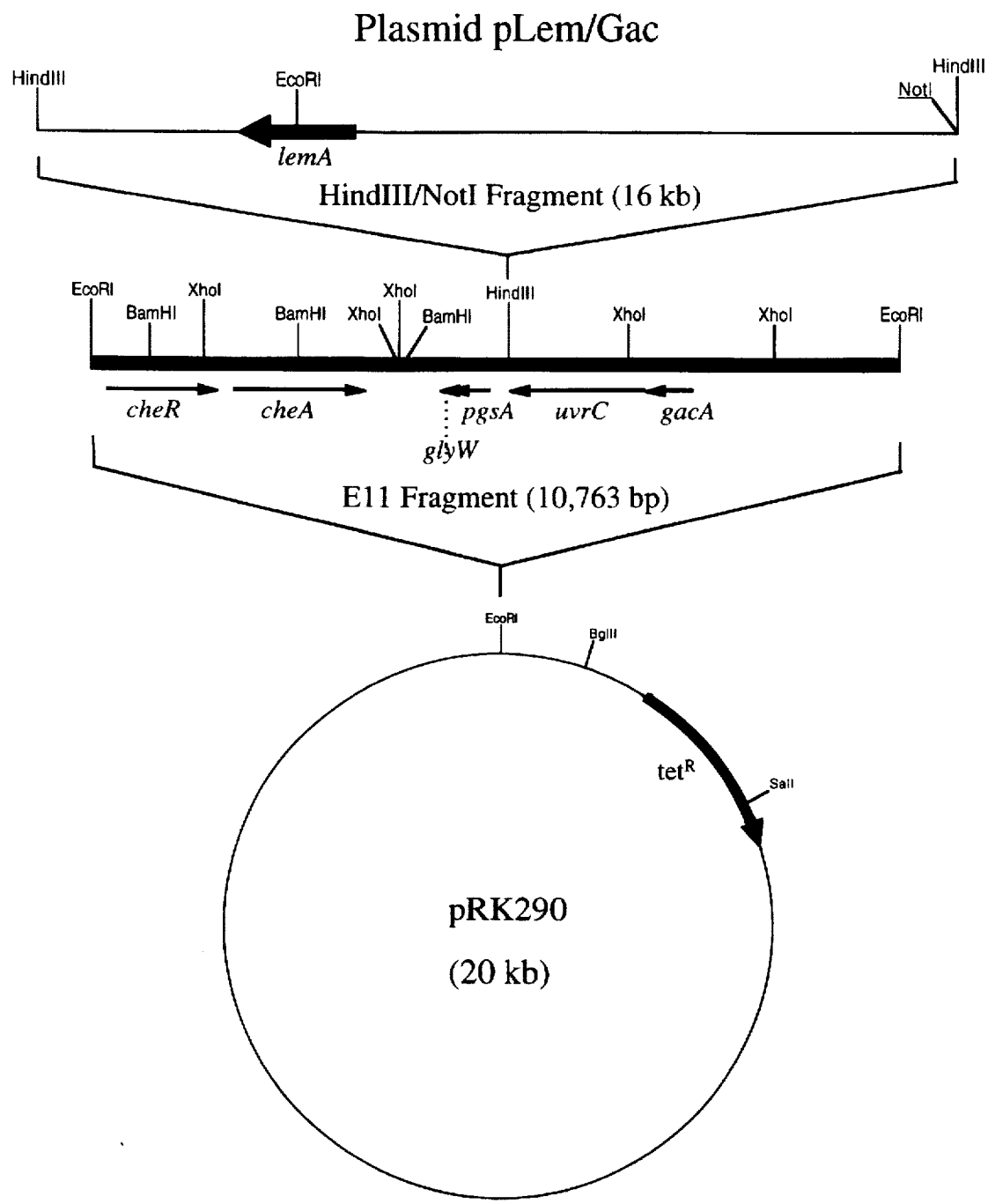
FIG. 4 is a plasmid map of plasmid pLem/Gac. The 16 kb HindIII fragment (upper shaded box) containing the lemA gene derived from *P. fluorescens* strain CGA267356 is shown in expanded view cloned into the HindIII site of the 11 kb EcoRI fragment (lower shaded box) derived from the same strain, and also shown in expanded view and cloned into the EcoRI site of plasmid pRK290. The positions of the genetic elements within the two fragments are indicated by arrows below each map.

The plasmid containing the lemA and gacA genes, pLem/Gac (FIG. 4), was constructed as follows: The plasmid pCIB146 (Examples 20 and 21 and FIG. 4 of U.S. Pat. No. 5,670,350) contains about 25-kb of chromosomal DNA from strain CGA267356. The lemA gene (see SEQ ID NO:8) has been described and shown to be located in this DNA. The subcloned DNA in pCIB 146 is flanked on each side by NotI and EcoRI sites. An approximately 16-kb HindIII/NotI fragment from pCIB 146, which contains the lemA gene, was excised from pCIB 146. The NotI end was converted to a HindIII site to facilitate cloning of the fragment into the unique HindIII fragment of plasmid pE 11 (Example 1; FIG. 1), which contains the gacA gene. Insertion of the 16-kb lemA-containing HindIII fragment into the HindIII site of pE11 did not disrupt the function of the gacA gene, because the HindIII site is not within its coding sequence.

New strain CGA364476 has been shown to produce higher amounts of the antifungal metabolite pyrrolnitrin (Table 1) and to have higher biocontrol activity (Table 2) compared to the related strain CGA267356.

EXAMPLE 6

Construction of *Pseudomonas fluorescens* Strain CGA375260 (gac*3)

Strain CGA375260 differs from the parent strain CGA267356 by a single base change within the coding sequence of the native gacA gene (SEQ ID NO:2). This modification was generated by introducing the native gacA gene into the hypermutagenic *E. coli* strain XL1-Red (from Stratagene, Inc.). The plasmid was recovered and introduced into a lemA mutant of strain CGA267356 that also contained lacZY genes inserted into an unknown chromosomal gene whose expression is regulated by LemA and GacA. Clones containing randomly mutated gacA genes that resulted in expression of the lacZY genes, as indicated by the formation of blue colonies on agar containing X-Gal, were further analyzed. These clones contained gacA genes that did not require phosphorylation by LemA in order to be active as a transcriptional activator. Three such gacA genes were isolated in this manner and the nucleotide sequence of each was determined. In each, there was a different single base change that resulted in a different single amino acid change in the encoded GacA protein. Each of the three modified gacA genes were used to replace the native gacA gene in strain CGA267356 by perfect site replacement mediated through homologous recombination.

Of the three, only one clone with a LemA-independent gacA gene (gac*) was shown to have enhanced pyrrolnitrin synthesis and biocontrol activity (Tables 1 and 2). The nucleotide sequence of the gac*A gene of this clone, CGA375260, was determined (SEQ ID NO:9) and it was found that a single base change occurs in codon 132, which is CAG and encodes a glutamine residue in the native GacA protein. The adenine base in this codon was changed to guanine to create a codon that encodes an arginine residue (CGG) in the altered strain. Therefore, the GacA protein (SEQ ID NO:10) in this strain has an arginine at amino acid 132 instead of the usual glutamine. In all other respects, this strain is identical to the parent strain. In the normal regulatory system and under the proper conditions, the LemA protein phosphorylates GacA and in the phosphorylated state it activates transcription of genes involved in the synthesis of antifungal compounds. This single base change in the GacA protein renders it active irrespective of the kinase activity of the LemA protein.

EXAMPLE 7

Construction of *Pseudomonas fluorescens* Strain CGA375259 (tac/gac pPrn)

Strain CGA375259 was derived from strain CGA267356 by replacement of the native promoter controlling expression of the chromosomal gacA gene with the tac promoter from *E. coli* (Example 3) and introduction of plasmid pPrn (Example 3).

The promoter of the gacA gene was replaced with the tac promoter as follows: A unique NruI site in the 2-kb XhoI gacA gene-containing fragment of pCIB137 (Examples 6 and 7 of U.S. Pat. No. 5,670,350) located 12-bp upstream of the translation start site of the gacA gene was modified by PCR to change it to a BamHI site. Plasmid pCIB 137 has been deposited with the NRRL and assigned accession number NRRL B-18981. A second BamHI site was inserted immediately 5' to the gacA translation start site using PCR. This created a small BamHI fragment immediately preceding the gacA coding sequence. This short BamHI fragment was excised and the DNA was religated to create a new BamHI site. The tac promoter was excised from plasmid pKK223-3 (FIG. 3 and SEQ ID NO:7) as a BglII/BamHI fragment and cloned in the appropriate orientation into the new BamHI site 5' to the beginning of the gacA gene, which was created by the excision of the above short BamHI fragment. This tac promoter/gacA gene (tac/gacA) fragment was excised as an XhoI fragment and was used to replace the native gacA gene on the 2-kb XhoI site in a plasmid containing the HindIII/EcoRI fragment from pE11. This plasmid was introduced into a gacA deletion mutant of strain CGA267356 (Example 9 of U.S. Pat. No. 5,670,350). Perfect replacement clones were generated (Example 9 of U.S. Pat. No. 5,670,350) and selected by restoration of the wild-type colony morphology. The newly inserted tac/gacA gene resulted in a higher level of expression of the gacA gene, compared to the low level of expression from the native gacA gene promoter.

Plasmid pPrn described in Example 3 above was subsequently introduced into the strain containing the tac/gacA gene to make strain CGA375259.

New strain CGA375259 has been shown to produce higher amounts of the antifungal metabolite pyrrolnitrin (Table 1) and to have higher biocontrol activity (Table 2) compared to the related strain CGA267356.

EXAMPLE 8

Construction of *Pseudomonas fluorescens* Strain CGA378584 (cPrn pLem/Gac)

Strain CGA3783584 contains the tac/prn ABCD gene cluster described in Example 3 in the chromosome and it also contains plasmid pLem/Gac described in Example 5.

The tac/prn ABCD genes were inserted in the chromosome of strain CGA267356 by modification of the *E. coli* cloning vector pKK223-3 by adding a kanamycin resistance gene derived from plasmid pUC4K (Pharmacea) into the PstI site of the multiple cloning site and by removing the EcoRI, NotI, and BamHI sites of pKK223-3. A 16-kb KpnI gene fragment derived from pCIB169 (FIG. 4 of application Ser. No. 08/258,261) was cloned into the modified pKK223-3. Plasmid pCIB 169 has been deposited with the NRRL and assigned accession number NRRL B-21256.

The prnABCD genes were deleted by digestion of the plasmid with EcoRI and NotI, conversion of the EcoRI and NotI ends to BamHI by fill-in, linkering, and religation. The 6.9-kb BglII fragment (Example 3), which contains the tac promoter/prnABCD/rrnB terminator construction, was ligated into the BamHI site, thus introducing these modified genes into the plasmid. This plasmid was introduced into strain CGA267356 by conjugation and the native prnABCD gene cluster was replaced with the tac promoter/prnABCD/rrnB terminator construct by homologous recombination.

Plasmid pLem/Gac (Example 5) was introduced into the strain with the chromosomally located tac promoter/prnABCD/rrnB terminator to create strain CGA378584.

New strain CGA378584 has been shown to produce higher amounts of the antifungal metabolite pyrrolnitrin (Table 1) and to have higher biocontrol activity (Table 2) compared to the related strain CGA267356.

EXAMPLE 9

Construction of *Pseudomonas fluorescens* Strain CGA267pPhz

This strain is the same as Pseudomonas strain CGA267356, except that strain CGA267pPhz contains a plasmid carrying DNA from a *Pseudomonas aureofaciens* strain that contains 5 genes known to encode the pathway for the biosynthesis of the antifungal metabolite phenazine-1-carboxylic acid (PCA).

Figure 5:
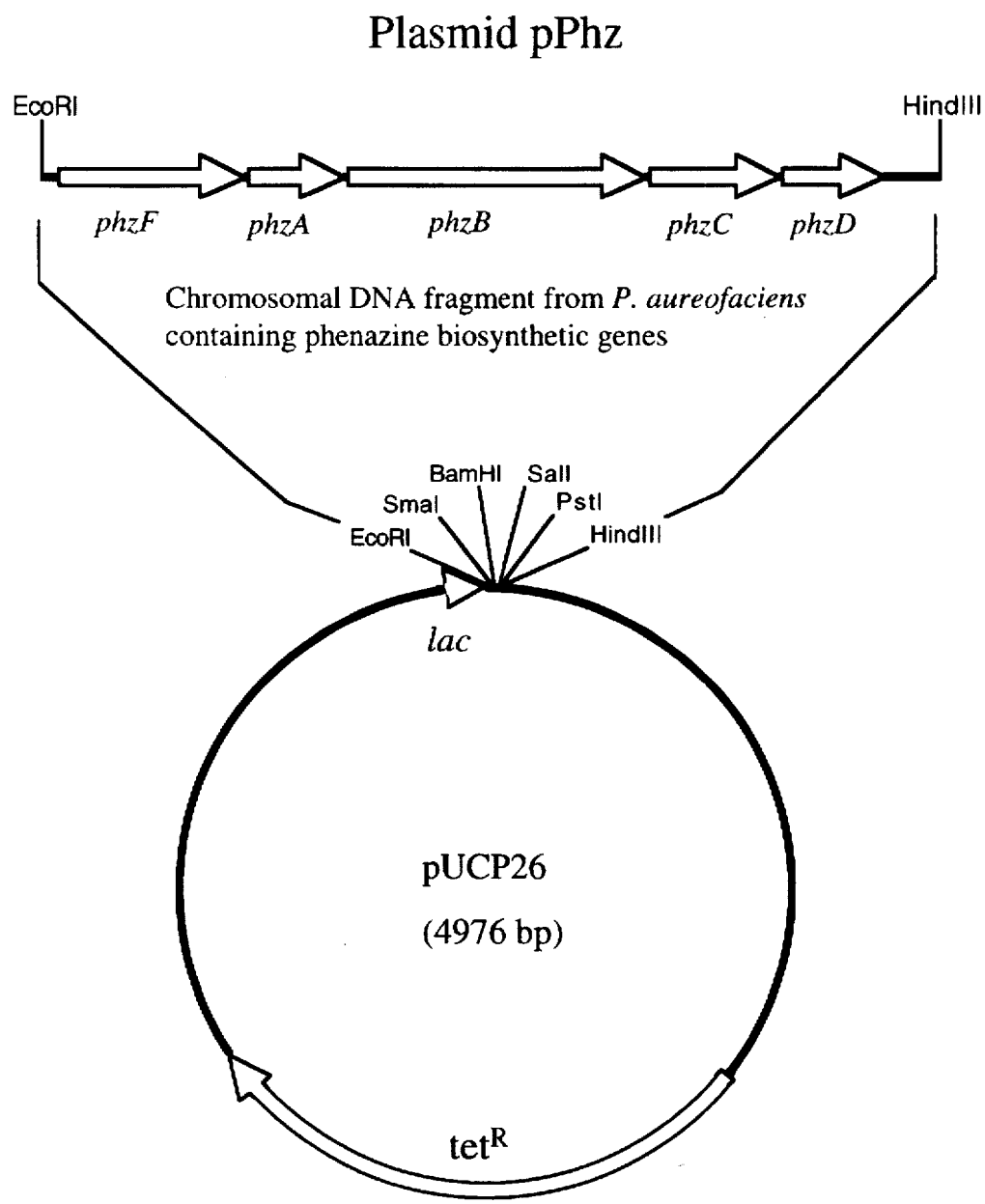
FIG. 5 is a plasmid map of plasmid pPhz. The 5.7 kb EcoRI/HindIII fragment containing the phzFABCD gene cluster (shaded box) derived from *P. aureofaciens* strain 30-84 is shown in expanded view cloned into the EcoRI-HindIII sites of the multiple cloning site in plasmid pUCP26. The lac promoter located adjacent to the multiple cloning site and the direction of its action are indicated by an arrow head. The positions of the genetic elements within this fragment are indicated by arrows below the map.

A 5.7-kb EcoRI/HindIII gene fragment (SEQ ID NO:11) containing the phzFABCD gene cluster from *P. aureofaciens* (Pierson, et al., FEMS Microbiol. Lett. 134:299–307 (1995)) was ligated into DNA of plasmid pUCP26 (West, et al., Gene 128:81–86 (1994)) that had been restricted with EcoRI and HindIII to create plasmid pPhz (FIG. 5). Plasmid pUCP26 is an *E. coli/Pseudomonas* shuttle plasmid that has a lac promoter flanking the multiple cloning site. The EcoRI and HindIII sites are oriented with the lac promoter such that the EcoRI site is closer to the promoter. Therefore, cloning of the EcoRI/HindIII phzFABCD gene fragment, in which the phz genes are cotranscribed on a single operon oriented in the EcoRI to HindIII direction into plasmid pUCP26, results in the proper juxtaposition of the lac promoter and phz gene cluster to cause expression of these genes from that promoter.

New strain CGA267pPhz has been shown to produce PCA, an antifungal metabolite not normally produced by parent strain CGA267356. It also produces the metabolites normally produced by the parent strain, including pyrrolnitrin.

EXAMPLE 10

Cultivation of Bacteria and Fungi for Screening Assays a. Cultivation of Bacteria The bacterial strains are stored in 20% glycerol at −80° C. prior to use. One loop from the stored culture is suspended in 5 ml Luria Broth (LB: 10 g Bacto-Tryptone, Difco; 5 g yeast extract, Oxoid; 0.25 g $MgSO_4H_2O$; 8 g NaCl; and 1 L distilled water; pH 7) and shaken at 150 rpm and 25° C. overnight. 100 ml LB is inoculated with 1 ml of the preculture and incubated under the same conditions. 10 ml of the last culture are centrifuged (10 min at 10,000 rpm), and the pellet is resuspended in 200 ml saline (0.8% NaCl) giving a concentration of approximately $10^8$ cfu/ml.

For exact determination, a dilution series ($10^0$ to $10^{-8}$, 20 μl in 180 μl) is prepared in microtiter plate and drops of 10 μl are spotted onto Luria Agar (LB with 1.5% Bacto-Agar, Difco) with an Eppendorf pipette. The cfu are counted after 24 hrs incubation at 28° C.

Antibiotics may be added if required for selection of bacteria: tetracycline~15 μg/ml; kanamycin~50 μg/ml.

b. Cultivation of *Rhizoctonia solani*

*Rhizoctonia solani* is grown on Potato Dextrose Agar (PDA, Difco) pH 5.6 in a petri dish. A 300 ml Erlenmeyer flask with 25 g millet and 50 ml distilled water is autoclaved and incubated with one agar plug (5 mm diameter) from a PDA culture of *R. solani*. After incubation at 20° C. in the dark for 3 weeks, the overgrown millet is air-dried and ground in a Culatti mill (1 mm sieve, 6000 rpm).

c. Cultivation of *Pythium aphanidermatum*

*Pythium aphanidermatum* is grown on Malt Agar (Oxoid), pH 5.6 in a petri dish. One agar plug (6 mm diameter) from this culture is transferred to a petri dish with 8 ml oatmeal agar (50 g Oatmeal, 3 ml 1.5% cholestrin in ethanol, and 1 L distilled water) with a slant surface. Two hrs later, 13 ml of sterile distilled water are added, and the plates are incubated for 10 to 14 days in the dark. The mycelium that grows from the agar surface into the water is transferred to a mixer and cut into small pieces. The concentration of oospores is counted in a Thoma chamber and adjusted with distilled water to $2 \times 10^4$/ml.

EXAMPLE 11

Assays For Biocontrol Activity

Preparation of bacterial cultures: All bacteria cultures are cultured in Luria broth for 2 days at 28° C. Bacterial cells are collected by centrifugation and resuspended in water to $10^9$ or $10^8$ bacterial cells/ml. 10 ml of each suspension is used to drench a pot containing 50 ml soil, resulting in $2 \times 10^8$ (high rate, CGA267356 only) or $2 \times 10^7$ cells/ml soil (all strains). Preparation of fungal inocula: *Rhizoctonia solani* is grown on twice-autoclaved millet seed until fully colonized, then air dried for several days. Dried inoculum is ground to a fine powder for use in all assays except the poinsettia assays, in which whole colonized millet seeds are used. A large supply of inoculum is stored at room temperature and used for several months. *Pythium aphanidermatum* is inoculated on twice-autoclaved millet seed and grown for one week. The colonized millet seed is air dried for 2 hours, then used immediately. Pythium[]i-infested millet seed is prepared weekly.

a. Pathosystem *Rhizoctonia solani*-cucumber

One cucumber seed is planted per pot containing a standard commercially available peat/bark type potting soil. The bacterial suspension is drenched on each pot and Rhizoctonia inoculum is broadcast over the surface of the soil. Each treatment in an experiment contains 5 sets of 12 plants which are randomized and placed in greenhouse under automatic sprinklers. Each experiment is repeated a minimum of three times. Stand counts are recorded at 1 and 2 weeks after planting and compared to uninfested and untreated healthy controls and infested and untreated diseased controls.

b. Pathosystem *Rhizoctonia solani*-impatiens

A single hole is drilled in the center of each pot and Rhizoctonia inoculum is broadcast over the surface of the soil and into the hole. One commercially purchased impatiens seedling plug is transplanted into the hole of each pot and bacteria suspension is applied as a drench. Each treatment in an experiment contains 5 sets of 12 plants which are randomized and placed in greenhouse under automatic sprinklers. Each experiment is repeated a minimum of three times. Stand counts are recorded at 1 and 2 weeks.

c. Pathosystem *Rhizoctonia solanli*-poinsettia

The bacterial suspension is drenched on strips of ten Oasis rooting cubes (the cell suspensions were adjusted so that each 50 ml cube was drenched with 40 ml of suspension), resulting in $2 \times 10^8$ or $2 \times 10^7$ cells/ml of cube, and one commercially purchased poinsettia cutting is inserted into each cube in the normal method for rooting. Five Rhizoctonia-infested millet seeds are placed in the middle of the strip (between plants 5 and 6), and the strips are placed in the greenhouse under automatic sprinklers. Each treatment in an experiment contains 4 rooting strips with 10 cuttings each and each experiment is repeated a minimum of three times. Stand counts are recorded at 10 days and 21 days after planting.

d. Pathosystem *Pythium aphanidermatum*-cucumber

One cucumber seed is planted per pot and the bacterial suspension is drenched on top of each pot. Pythium inoculum is broadcast over the surface of the soil and replicates are randomized and placed in the greenhouse under automatic sprinklers. Each treatment in an experiment contains 5 sets of 12 plants and each experiment is repeated a minimum of three times. Stand counts are recorded at 1 and 2 weeks.

EXAMPLE 12

Extraction of Antifungal Metabolites

Active antifungal metabolites such as pyrrolnitrin (prn) can be extracted from the growth medium of bacterial strains that produce inhibitory antibiotics. For example, using strain CGA376146, this can be accomplished by extraction of the growth medium with 80% acetone followed by removal of the acetone by evaporation and a second extraction with diethyl ether. The diethyl ether is removed by evaporation and the dried extract is resuspended in a small volume of methanol. Alternately, the antifungal metabolites can be extracted with methanol using conventional methods. Small aliquots of the antibiotic extract applied to small sterile filter paper discs placed on an agar plate will inhibit the growth of Rhizoctonia solani, indicating the presence of the active antibiotic compound.

EXAMPLE 13

Combination of Biocontrol Strain with Fungicides

The biocontrol strains of the invention are each applied to non-sterile soil as a drench at $2 \times 10^8$ cfu/ml soil, while metalaxyl fungicide is either drenched (Ridomil at 0.02, 0.5, or 2 ppm) or coated onto seeds (Apron at 35 g a.i./100 kg seed). *Pythium aphanidermatum* is introduced as an oospore suspension (1400 spores/ml soil). *Rhizoctonia solani* is introduced as a pelleted millet powder (5 mg in the center of each pot). After incubation for 19 days in the greenhouse, the hypocotyls of cotton seedlings are rated for disease on an observation scale.

Almost complete control of damping-off may be achieved when one of the biocontrol strains is applied together with Ridomil at 2 ppm. Using Apron instead of Ridomil results in the same level of control. Each of the biocontrol strains alone still gives significant suppression of both pathogens. Metalaxyl fungicide alone, however, fails to control the disease complex. 0.2 ppm Ridomil alone gives approximately 40% suppression of *Pythium aphanidernatum*. However, the combination of 0.02 ppm Ridomil with one of the biocontrol strains significantly increases the level of control. Thus, the combined application of the biocontrol bacterial strains of the invention with a reduced rate of metalaxyl fungicide achieves almost complete control of the seedling disease complex in cotton caused by *Rhizoctonia solani* and *Pythium aphanidermatum*.

EXAMPLE 14

Antifungal Compositions

Formulations of antifungal compositions containing as the active ingredient the antifungal metabolites that are produced by the biocontrol strains of the invention and that are inhibitory to the growth of Rhizoctonia and Pythium are produced according to Examples 10 and 11 in U.S. Pat. No. 5,348,742. These formulations include emulsifiable concentrates, solutions, granulates, dusts, wettable powders, extruder granulates, coated granulates, and suspension concentrates.

The antifungal compositions may be used to control or inhibit the growth of a plant pathogenic fungus by applying an effective amount of the biocontrol composition to an environment in which the fungus may grow, to a plant or plant part, and/or to seed.

EXAMPLE 15

Field Trial of Biocontrol Strains

Cultures of the biocontrol strains are stored in 20% glycerol at −80° C. One loop from the stored culture is suspended in 5 ml Luria Broth (LB: 10 g Bacto-Typtone, Difco; 5 g yeast extract, Oxold; 0.25 g $MgSO_4H_2O$; 8 g NaCl; and 1 L distilled water; pH 7) and shaken at 150 rpm and 25° C. for 24 hrs. 100 ml LB is inoculated with 1 ml of the preculture and incubated under the same conditions. After 16 hrs, the culture is centrifuged for 10 minutes at 10,000 rpm, and the pellet is resuspended in saline (0.8% NaCl) and adjusted to $3 \times 10^9$ cfu/ml (OD2). Thus, 100 ml of culture will give approximately 200–300 ml drench of OD2.

A hemocytometer and/or spectrophotometer is used to adjust the concentration of bacteria in the drench. Otherwise, a standard salt solution of a known OD (e.g., Phillips' Milk of Magnesia™=$Mg(OH)_2$) can be used to adjust the OD of the drench. If a centrifuge is not available, the whole culture broth has to be applied; a hemocytometer is then used to determine the cfu/ml.

For exact determination, a dilution series ($10^0$ to $10^{-8}$; 20 μl in 180 μl) is prepared in a microtiter plate and drops of 10 μl are spotted onto Luria Agar (LB with 1.5% Bacto-Agar, Difco) with an Eppendorf pipette. The cfu are counted after 24 hrs incubation at 28° C.

250 mL of the bacterial suspension per 10' (=1 rep) are drenched onto the covered seeds (200 seeds per rep). A handheld sprayer or watering can free of pesticide residues is used to apply the drench in a narrow band of approximately 1.5 inches width.

Rhizoctonia and Pythium are prepared for inoculation as in Examples 10 and 11 above.

Emergence is recorded at 10 days after planting to assess pre-emergence damping off. Stands are recorded at 21 days and 28 days after planting to assess post-emergence damping-off.

While the present invention has been described with reference to specific embodiments thereof, it will be appreciated that numerous variations, modifications, and embodiments are possible, and accordingly, all such variations, modifications and embodiments are to be regarded as being within the scope of the present invention. Furthermore, all publications and patent applications mentioned in this specification are indicative of the level of skill of those skilled in the art to which this invention pertains. All publications and patent applications are therefore hereby incorporated by reference to the same extent as if each individual publication or patent application was specifically and individually indicated to be incorporated by reference.

TABLE 1

Pyrrolnitrin production by *P. fluorescens* strain CGA267356 and genetically modified strains derived from it. Pyrrolnitrin was isolated from 3 day old cultures of the strains grown in CMMMAD medium by extraction with methanol and quantified by HPLC analysis.

| Strain | Pyrrolnitrin (mg/L) |
|---|---|
| CGA267356 | 21.6 |
| CGA376146 | 51.3 |
| CGA364473 | 47.0 |
| CGA375258 | 78.5 |
| CGA376148 | 87.2 |
| CGA364476 | 97.1 |
| CGA375260 | 46.3 |
| CGA375259 | 70.6 |
| CGA378584 | 122.4 |

TABLE 2

Biocontrol activity of *P. fluorescens* strain CGA267356 and genetically modified strains derived from it. The data presented is the control of Rhizoctonia on three plant types and Pythium on cucumbers only. All data is presented relative to the parent strain, CGA267356, applied at high (=100% biocontrol activity) and low (=0% biocontrol activity) rates equal to $2 \times 10^8$ and $2 \times 10^7$ cells/g soil, respectively. All other strains were applied only at the low rate so that any relative biocontrol activity greater than 0 represents an improvement compared to the parent strain. All data are the mean of three experiments.

| | Relative Biocontrol Activity | | | |
|---|---|---|---|---|
| | Rhizoctonia | | | Pythium |
| Strain | Cucumber | Impatiens | Poinsettia | Cucumber |
| CGA267356 High Rate | 100 | 100 | 100 | 100 |
| CGA267356 Low Rate | 0 | 0 | 0 | 0 |
| CGA376146 | 34 | 67 | 29 | 33 |
| CGA364473 | 13 | 88 | 43 | 57 |
| CGA375258 | 87 | 67 | 61 | 32 |
| CGA376148 | 28 | 68 | 133 | 4 |
| CGA364476 | 60 | 0 | 75 | 133 |
| CGA375260 | 102 | 0 | 47 | 83 |
| CGA375259 | 60 | 33 | 52 | 51 |
| CGA378584 | 115 | 45 | 54 | 0 |
| CGA267pPhz | 53 | 10 | 0 | 50 |

DEPOSITS

The following strains were deposited with the Agricultural Research Service, Patent Culture Collection (NRRL), 1815 North University Street, Peoria, Ill. 61604, on Sep. 5, 1997, under the Budapest Treaty on the International Recognition of the Deposit of Microorganisms for the Purposes of Patent Procedure. All restrictions on the availability of the deposited strain will be irrevocably removed upon the granting of a patent.

| Strain | Accession Number |
|---|---|
| CGA376146 | NRRL B-21811 |
| CGA364473 | NRRL B-21812 |
| CGA375258 | NRRL B-21813 |
| CGA376148 | NRRL B-21814 |
| CGA364476 | NRRL B-21815 |
| CGA375260 | NRRL B-21816 |
| CGA375259 | NRRL B-21817 |

5,756,087

-continued

| Strain | Accession Number |
|---|---|
| CGA378584 | NRRL B-21818 |
| CGA67pPhz | NRRL B-21819 |

---

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
    ( A ) LENGTH: 10763 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Pseudomonas fluorescens
    ( B ) STRAIN: CGA267356 (aka MOCG134 and aka BL915)

( v i i ) IMMEDIATE SOURCE:
    ( B ) CLONE: Plasmid pE11

( i x ) FEATURE:
    ( A ) NAME/KEY: misc_feature
    ( B ) LOCATION: 210..1688
    ( D ) OTHER INFORMATION: /product="methyltransferase"
      / note="Coding sequence for methyltransferase has
      homology to the cheR and frzF genes from E. coli and
      Myxococcus xanthus, respectively."

( i x ) FEATURE:
    ( A ) NAME/KEY: misc_feature
    ( B ) LOCATION: 1906..3633
    ( D ) OTHER INFORMATION: /product="sensor kinase"
      / note="Coding sequence for sensor kinase has
      homology to the rcsC, frzE, and bvgS genes of E. coli,
      M. Xanthus, and Bordittella pertussis, respectively."

( i x ) FEATURE:
    ( A ) NAME/KEY: misc_RNA
    ( B ) LOCATION: complement (4616..4691)
    ( D ) OTHER INFORMATION: /product="tRNA"
      / note="(complementary DNA strand) Homology to glyW from
      E. Coli."

( i x ) FEATURE:
    ( A ) NAME/KEY: misc_feature
    ( B ) LOCATION: complement (4731..5318)
    ( D ) OTHER INFORMATION: /product=
      " CDP-diacylglycerol-glycerol-3-phosphate-3-phosph
      atidyltrans."
      / note="Coding sequence for
      CDP- diacylglycerol-glycerol-3-phosphate-3-
      phosphatidyltransfere se has homology to pgsA."

( i x ) FEATURE:
    ( A ) NAME/KEY: misc_feature
    ( B ) LOCATION: complement (5574..7397)
    ( D ) OTHER INFORMATION: /product="UVR exonuclease subunit
      C"
      / note="Coding sequence for UVR exonuclease subunit C -continued has homology to uvrC."

( i x ) FEATURE:
(A) NAME/KEY: misc_feature
(B) LOCATION: complement (7400..8041)
(D) OTHER INFORMATION: /function="response
regulator/transcription activator"
/ product="gacA (aka gafA)"
/ note="Coding sequence for gacA (aka gafA) has homology
to the uvrY and gacA genes of E. coli and Ps.
fluorescens, respectively."

( x i ) SEQUENCE DESCRIPTION: SEQ ID NO:1:

```
GAATTCGATG ACATGCCGCG CGCCGGCATC GACACGCAAA TGGTCGACCT GGTGCTGCCG      60
GTGGTCGAAA TGCCGCAGAA GCTGCTGGAG CTGTGGCGCA ACTCTCAGCT CATCACCCTG     120
CCGACCGCCA ACGATCCGCA AATCAAGGTC TCGGCGCCGG TGTCCAAACG CGATGCCGCG     180
GCGGCGAACA GCAGCTGCAA GACATCCTGA TGCTGTTGCG CACCGGCACC GGCCATGACT     240
TCAAGCATTA CAAGCGCGCC ACGGTGCTGC GGCGGATCGA GCGCCCGCTG CAGGTCACCG     300
CCCAGCCGGA CCTCGCCGCC TATCACGATT ACCTGCAGAT GCACCCTGAA GAAACCAAGG     360
CGCTGCTGGG CGACATGCTG ATCGGCGTGA CCAATTTCTT TCGCGACCGC GAGGCCTTCG     420
AAGCCCTGGA GCGCAATGTC ATTCCTGCCC TGGTGAAGTC CTTGCAGGAC AGCCAACCGC     480
ACCGTGAAGA CGTGCGCATC TGGTCCGCCG GCTGCTCCAC GGGTGAAGAG GCCTATAGCC     540
TGGCAATCGT CGCCAGCGAG CAGATGGCCC TGGAGGCCTG CAACGCCAAG CTGCAGGTAT     600
TCGCGACCGA TATCGACGAT CGTGCCATCG CCCAGGGACG CAAGGGGGTC TATCCCGAAG     660
CGATCGTTAC CGATGTGCCT CCGCAGCGCA TGCGCCAGTA CTTTTCCCGG GAAAACCAGC     720
ATTACCGGGT GCGCAAGGAG ATTCGCGAAA AGGTGCTGTT CGCCAAGCAC AGCCTGCTGG     780
CGGATCCGCC ATTTTCGCAG ATCGACTTGA TCGTCTGCCG TAACCTGCTG ATCTACCTGG     840
ACCGCGACGT GCAACGGGAG ATCCTGCAGA TGTTCCACTT CGCCCTGCGT CCTGGAGGCT     900
ACCTGTTCCT CGGTTCCTCC GAATCCGCGG ACGGCTGCCA GGATCTGTTC GTGCCGGTCG     960
ACAAGCGCAA CCGCATTTTC CGGGTACGGC CCAACTCGGC CACGGTTCGC CGCGCGCCCA    1020
CCATGCCGCG ACGGCGTACA TGCGCACCAT CGGCAGCCCC CACCCCGTGG AAACCAAGTG    1080
TCTCGCGCAA AACCTCGTTC GCCGACATCC ACCTTCGCGC CCTGGAAAAG TGCGCGCCGC    1140
CGAGCATGAT CGTCGATGCC AACGCCGACA TCCTGCACAT GAGCGAAGGC GCCGGCCGGT    1200
TCCTGCGCTA TGTCGCGGGG GAAATCACCC GCAACCTGCT GACCCTGATC CAGCCCGAGC    1260
TGCGCCTTGA ACTGCGCACC ACGCTGTTCC AGGTGCAACA GTCCGGTGTT GCGGTGACCG    1320
CCGCCGGGTG CGCATCGAGC GGGAAAAGAA GCCTTGTTTC ATCGACCTCA CAGCCCGCCC    1380
CTTCAAGGAC GAGGAAACCG ACAACGAATA TGTGCTGGTG GTGTTCGAGG AGACCGAGGC    1440
CGACCCACGG GAGCTGCGCG AGACCAGCGC CAGCCAGACG GAAAACCAGA TGCTGGCCAA    1500
CCTCGAGCGG GAGTTGCAGC GGACCAAATT GCACCTGCAG GACACCATCG AGCAATCGGA    1560
AGTCTCCAGC GAGGAGCTCA AGGCGTCGAA CGAAGAAATG CAGGCGCTCA ATGAAGAGCT    1620
GCGCTCGGCC ACCGAAGAGC TGGAAACCAG CAAGGAAGAG TTGCAGTCGA TCAATGAAGA    1680
GCTGCTGACG GTCAATTACG AGCTGAAAAC CAAGGTCGAG GAAACCGACA AGATCAACGA    1740
CTACCTGACC AACCTGATCG CCTCCACCGA CATCGCCACG GTGTTCGTCG ACCGCAACAT    1800
GCGCATCCGC TGGTTCACCC CGCGCGCCAC CGACATTTTC AGCATGCTGC CGGTGGACAC    1860
CGACGCTCAT TACTGGACAT CACCCACCGC CTGAACTACC CGGAAATGGC CGAGGACGCC    1920
GCGACCGTGT TCGAGTCGTT GAGCATGATC GAGCGTGAAG TCAACAGCGA CGATCAGCGC    1980
```

```
TGGTACATCG CACGCCTGTT GCCCTATCGC TCCAGCGAAG ACCATATCGA CGGCACCGTG    2040
CTGACCTTCA TCGATATCAC CAAGCGCCGG CTGGCCGAGG AGGAACTGCG CCTGGGCGAA    2100
GAACGCATGC GCCTGGTCGC CGAAAGCACC CATGATTTCG CCATCATCAT CCTCGACAAC    2160
CAGGGCCTCA TCACCGACTG GAACACCGGG GCGCAACTGA TCTTCGGCTA TACCAAGGAC    2220
GAAGTGCTGG GCGCCTATTA CGACCTGATT TTCGCGCCTG AGGACCGCGC CGGCGGCGTG    2280
CCGGAAAGCG AGCTGCTCAC CGCCCGCGAA CACGGCCGCA GCGACGATGA ACGCTGGCAT    2340
ATACGCAAGG ACGGCGAGCG CTTTTTCTGC AGCGGCGAAG TCACGCGGCT CAAGGGTGAC    2400
AGCCTGCAAG GCTACGTGAA AATAGCCCGC GACCTGACGG GCCACAAACG CATGCAGGAC    2460
GAGCAGAACC AGAAGCTGAT GGAGACCCAG ACCCACAGCC ACCTCAAGGA TGAGTTTTTC    2520
GCGGTGATGT CCCATGAACT CAAGCATCCG CTCAACCTGA TCCAGCTCAA CGCCGAGTTG    2580
CTGCGTCGCC TGCCGACGAC CAAGGCGGCC GCCCCTGCCC TCAAGGCGGT CAATACCATT    2640
TGCGAGGCTG TCTCCAGCCA GGCGCGGATC ATCGACGACC TGCTGGATGT GCGGCGTTTG    2700
CGCACCGGCA AGCTCAAGCT GAAGAAACAG CCGGTGGATC TTGGCCGGAT CCTGCAGGAC    2760
ATCCATACCG TGGTGCTCAG CGAAGGGCAT CGCTGCCAGG TGACGCTGCA AGTGCCGTTG    2820
CCACCGCAAC CGCCGTTAAT GATCGATGCC GATGCGACGC GGCTGGAGCA GGTGATCTGG    2880
AACCTGGTGA ACAACGCCCT GAAATTCACC CCGGCCAATG GCTTGGTCCA GTTGATCGCC    2940
CAGCGGGTCG AGGATAAGGC GCACGTGGAT GTCATCGACA GCGGCGTGGG CCTGGCCGAG    3000
GAAGACCAGA ACAAGGTGTT CGACCTTTTC GGCCAGGCGG CCAACCAGCA CGGCACTCAT    3060
CAACGCGACG GGCTGGGCAT CGGCCTGTCA CTGGTGCGCC AGCTGGTGGA AGCCCACGGC    3120
GGCTCGGTCA GCGTGCAGTC GAAGGGGCTG GGCCAGGGAT GCACCTTTAC CGTGCTCTTG    3180
CCCCTGAGCC ACCCCAACGA CAGCGCTCCC AAACAGCCCG CGTCGCGGGG TGTCGAACGC    3240
CTTGCCGGCA TCAAGGTGCT GCTGGTGGAC GACTCGCGGG AAGTCATGGA AGTCCTGCAA    3300
CTGCTGCTGG AGATGGAGGG CGCGCAAGTC GAGGCCTTCC ACGACCCGCT GCAGGCCTTG    3360
GGCAATGCCA GGAACAACAG TTACGACCTG ATCATTTCAG ACATCGGCAT GCCGATTATG    3420
AACGGCTACG AACTGATGCA GAACCTGCGC CAGATCGCTC ACCTGCACCA TACGCCAGCG    3480
ATTGCGCTGA CCGGTTACGG CGCCAGCAGC GACCAGAAGA AGTCCCAGCA TGCGGGATTC    3540
GATCGGCATG TGAGCAAACC CGTGGCTCAG GACCCGCTGA TCGACCTGAT CAGGGAGCTG    3600
TGCAGCCAGG GCTTGCGCTC GGCTGAGCAC TGATGGTCTA GACCCGGCGA ACCCACCTCG    3660
TCGGCCTTGA GCGCGGCGAG CGCCATTGCC TGCTGGGCAG CTATTCACGC TTGCGGATCG    3720
TCGCGCCTGC GGGCCACCGC CTCTTTGATG GCTTGCTCAT AGGCGGCGTT GGCCTGGTCC    3780
TTGAGCTTGA GCCAATCGTC CCAATCGATC ACGCCGTTGC GCAGCAACTC CTCGGCCGCG    3840
CTTAACAGCG CCTGATGCCA GGCGTCCGGC GAGCCGGAAC GGTAGTCACG GTCTTCCAGC    3900
AGGCCTTGCC AGGCGTCCAG TTCCGGTGTC TTGCGTTCAT TGACCATGGC AGCCACGGCC    3960
TTTGTTCATT GCCGATAAAT CGGCGAGTGG GTGGTGGGTT CTCGGATAT GCGCCCTGTC     4020
CTGCTCGAGA ACGGCCAGGC CGGGACATTG CTCAACGGTC AGCGACCGGA TGGAGCTCGA    4080
GCGGCATGCC ATCGACCAGC GTCAAGGTCA GGTTCTCGAT GGTGCCGGCG ATCCGGTCCT    4140
TGAATACCGG TTCGCCGTCC GGATCCAACT CATCGTAGAA AAAGCGCGTG CCTTCGAGCC    4200
AGCCAATGGT CGTTTGCAGG TCCGGCCCCA GGTAATACTT GCCGTCAAGG AAAAACCCGG    4260
TAAAGGGCTC CACCCGCTCG CGATTCTCAA TGACATAACG TATTCCAGCG TGCATACCTG    4320
TCGATTTATC GAGCATGGCG TCGATCTCCC AGCAGATGAA TCCGGTAGAC CGCGTGGCTT    4380
```

-continued

```
TTTCACTGTT CCTTTTGATT GCCCGCCCGA CGCTGGCGAG CCTTGCTCGC GCGTCCTGGC    4440
CGCATTGCGC GGCGAATGGG CGACGTCGAA TCCGATCTGC AAGTGCCCAG CTAGCGGCCC    4500
GGCCACGGCA ATACGGGCTT CAGGTACGGC TTAGAAAGAA GAATGACGAT TGGCTCGACA    4560
TATTTTTTGG CGCAAAAAAA AATGGACCTC TTTTCAGAGG TCCATTTTTA ATATTTGGAG    4620
CGGGAAACGA GACTCGAACT CGCGACCCCG ACCTTGGCAA GGTCGTGCTC TACCAACTGA    4680
GCTATTCCCG CGTCTTGGTG GTGTGCATTT TATAGAAATT CGAAACTGCG TCAACCCCTT    4740
GATTCAAAAA GTTTTATTTC TTTTCTACCA TCGGTCTTCA GGTGCGGCCA GGCAGCGCGC    4800
AGGTACTGCA ACATCGACCA CAGGGTCAGC CCTCCGGCGA TCAGCAGGAA GGCATAACCC    4860
AGCAGCACCC AGAAGGTGAA GGCCGGCGGA TTGGCCAGCA GGATCACCAG CGCCAGCATC    4920
TGCGCGGCAG TTTTCCGATT TGCCCATGTT GGACACCGGC CACCTGGGCG CGTGCGCCCG    4980
AGCTCGGCCA TCCACTCGCG AAGGGCGGAC ACCACGATTT CACGCCCGAT GATCACCGCT    5040
GCCGGCAGGG TCAGCCACAG GTTGCCGTGC TCTTGCACCA GCAGCACCAG GGCCACCGCC    5100
ACCATCAACT TGTCGGCCAC CGGATCGAGG AAGGCCCCGA ACGGCGTGCT CTGCTCCAGA    5160
CGCCGCGCCA GGTAGCCATC AAGCCAGTCG GTGGCCGCGG CGAACGCAAA GACGGAACTG    5220
GCGGCCATGT AGCTCCAGTT GTAAGGCAGG TAAAACAGCA AAATGAAGAT CGGGATGAGC    5280
AGAACGCGTA GAACGGTGAT CAGATTAGGG ATATTCATCG GCACAACTGG CTACGAGGTG    5340
AGTGGCAATC TACTCGGAAA AGACAGCAGA TGAGGTAGCA CGGCCATTCT ACGGGCTTCT    5400
GCCACAGCGT GTCTAACACT GTTCCAAGAC TTCGGGCCGC TCGAAAGAGC AACTTCAGAA    5460
GGTCTACACG CGCAAAATAA GACATTCAGT TCTTCTGTAA GTACCGTGTA GATCGGGATC    5520
TATCAGCGGT GCCCCGCCAA AAAGGAAGCC TTGAAGCTTC CTTGAGCGCT CCCCTACTCG    5580
CTATGCAAGT TCGCATAAAT CAGCTCAGCG AGCTTTTTAC TGATCCCCGG CGCTTTGGCG    5640
ATCTCCTCAA TGCTGGCGCG AGACAGTTCC TGCAACCCAC CAAAGTGTTT CAACAGGTCG    5700
CGGCGGCGCT TGGGGCCGAC GCCGGCCACG TCTTCGAGGG TCGAAGTGCG GCGGGTCTTT    5760
CCGCGACGGG CGCGGTGGCC AGTGATGGCG AAACGGTGAG CCTCGTCGCG GATCTGCTGG    5820
ATCAGGTGCA GCGCCGGCGA GTCGCCCTTG AGGGTGAACT CATGGGCGGC ATCGTTGAGG    5880
TAGAGGGTCT CGAAACCGGT CTTGCGCGTC GCACCCTTGG CCACACCCAG CAGGATCAGG    5940
TCAGGCACCG CCAACTCGTT GAGCACGTCG CGGGCCATGG ACAGCTGGCC CTTGCCGCCG    6000
TCCACCAGCA GGATGTCCGG CAACTTGCCC TCGCCGTCCT TGAGTTTGCT GAAGCGTCGT    6060
GTCAGGGCCT GGTGCATCGC CGCATAGTCA TCGCCGGCGG TGACGCCTTC GATGTTGTAG    6120
CGCCGATAGT CGGACTTCAG CGGCCCTTCC GGACGAACA CCACGCAGGA CGCCACGGTC    6180
GCCTCGCCGC TGGAGTGGCT GATGTCGTAG CACTCCAGGC GTTGCGGTGG CTCGTCCAGG    6240
TTCAGCACTT CGGCCAGGGC CTCGAAACGC GCCGCCACAT GCTGCCGGTT GGCCAGGCGC    6300
GCACTCAGCG CCTGTTCGGC GTTGGTCACT GCCAATTGCT GCCAGCGCGC CCGCGTACCG    6360
CGCACCCGGT GGCTGATGCT CAGCTCGCGG CCACGCAGCT CCTGGATCGC CGCGATCAGG    6420
GCCGGGAAAT CCTCATGGAC CACGTTGACG ATCAGCTCGC TGGGCAGGTC GCGCTCCGGG    6480
CTGCTGAGAA AGTACTGGCC GAGGAAGGCC GACATGACTT CGGCCACCTC TTCCTCGATG    6540
CCCACCTGGG GAAAGAAGTT CTTGCTGCCC AGCACCCGCC CGCCCGCAC GCTGATCAGG    6600
TGCACACAGG CGCCGCCCGG GTTGACGAAG GCCGCGACCA CGTCGACGTC GCCACTGCCG    6660
CCTTCCATGC TCTGCTGGTC CTGGACCCGT CGCAGCAGGG AAATCTGGTC GCGCAGCTCA    6720
GCGGCCTTTT CGAAGTCCAG GGTGCTGGCC GCCTGCTCCA TGCCGGCCGA CAGTTCGTCG    6780
```

| | | | | | |
|---|---|---|---|---|---|
| GTCAGGGCAT | TGCTGCGGCC | TTCGAGGAAC | ATCACCGAGT | GGCGCACATC | CTCGGCGTAC | 6840 |
| ACCTCGGCCT | CCACCAGGCC | GACGCACGGC | GCCTTGCAGC | GCTTGATCTG | ATATTGCAGA | 6900 |
| CATGGCCGGG | TGCGGTTCTT | GTAGTAGCTG | TCCTCGCACT | GGCGGACCAT | GAAGGTCTTT | 6960 |
| TGCAGCAGGC | TGAGGCTCTC | GCGAATGGCC | CCGGCGCTGG | GGTACGGGCC | GAAATACTTG | 7020 |
| CCCTTCTGCT | TCTTCGCCCC | ACGATGGATG | CTGAAACGCG | GAAACTCGCC | GTCGAGAGA | 7080 |
| AACACATAGG | GATAGGACTT | ATCGTCGCGC | AGCAGGATGT | TGTACGGCGG | CCGCCATTCC | 7140 |
| TTGATCAGCG | TCTGCTCGAG | CAGCAGGGCT | TCGGTCTCGT | TGGCGGTGAT | GGTGGTTTCG | 7200 |
| ATCTGCGCGA | TGCGCCCCAC | CAGGGCAGCG | GTCTTGGGCG | CCAGGCCGGT | CTTGCGAAAG | 7260 |
| TAGCTGGCCA | GGCGGCTCTT | CAGGTTCTTG | GCTTACCGA | CGTACAGCAG | ACGCGTATCG | 7320 |
| CTGTCGAACA | TGCGATACAC | GCCAGGACGG | CCACTGCAGG | TGGAAAGAAA | AGCACTGGGA | 7380 |
| TCAAACGGGT | CGGTCATTGT | CAGGCACTGG | CATCGACCAT | GCCGTGGCGA | ACCGCCAGCA | 7440 |
| ATGTCAGTTC | AACATCGCTG | CTGATCGAGA | GCTTTTCGAA | GATGCGGTAA | CGGTAGGTAT | 7500 |
| TAACGGTTTT | CGGAGACAGG | CACAGCTTGT | CGGAGATGAT | CTGCACTTTC | TGGCAGCCGA | 7560 |
| CAATCATCAG | CGCGATCTGG | ATTTCCCGCT | CGGACAAAGC | ATCGAACGGT | GAATCACTGG | 7620 |
| AAGGCTGGAA | TGACTTGAAC | ACCAACTGCT | GGGCAATTTG | CGGGCTGATG | TAACGCTGGC | 7680 |
| CGGCAAACAC | CAGGCGAATG | GCCTGCACCA | TTTCATTGAG | GCCCGCCCCC | TTGGTCAGGT | 7740 |
| AACCCGCCGC | GCCGGCTTGC | AGCAAGCGGG | TCGGAACGG | ATCTTCTTCA | CACACGGTGA | 7800 |
| CGGCCACGAC | TTTGATATCC | GGGTGACTGC | GCAACAATTT | GCGCGTGGCT | TCAAGACCGC | 7860 |
| CGATCCCGGG | CATCTTGACG | TCCATGAGGA | CCACATCGGG | TTTCAACTCC | CGGGCCTTGA | 7920 |
| GCAGGGATTC | CTCCCCTGAC | TCGGCCTGGC | CGACCACTTG | CAGGCCATCG | ATGTCAGCCA | 7980 |
| GCATTCGTGT | AATACCTGTA | CGAACGAGAT | CATGGTCATC | GACTACTAGC | ACCCTAATCA | 8040 |
| AGCAGACACC | TCGCGATTTG | GGTCTTATAG | GTTGCCGGAC | ACCTTAGCAA | AAAAGCAGCG | 8100 |
| TGCTGACCTA | ATGACAAACA | CCATATAAAA | AGCACTTGTT | CATCAGGGGT | ATCCGGTGGA | 8160 |
| TGGTTGATGC | GCTGCGAACG | CCCTGCCCTA | AGGCTCTCGG | GCGTCCGCCT | TTCTTTTCAT | 8220 |
| GAGGCTGGAA | ACCGAAAGCT | CGGCAAGGGT | ATGGGTCAGG | TGCCGGATCG | CGTCCTGATC | 8280 |
| TTCCTTGTAC | AAGGCCCGGA | TAACTGACGA | GGCTTTTCTC | TTCGCTCTGG | CTGAGATTCT | 8340 |
| CAGCCCTGGT | CGGGGTCCGC | CTGCCGGTCA | CTATATAAAG | GACATCGACC | CCTTTTGTCG | 8400 |
| CCACCCGGGA | CAAGTAATCC | GCCTTGGGCA | CACGGTCTCC | ACTTTCATAT | CTGCCTTGGG | 8460 |
| CATTGGCTTC | CACGCCGCCA | ACTTCACCAA | ATTTTTTCTG | CGACAACCCC | AGGCGTTCCC | 8520 |
| TTTCCTGTCG | TCAACCGCGA | ACCGATTCCA | CTCATTGGA | TGTATGATCC | TTTTTATGC | 8580 |
| ACCCCTAGGG | GTGTTACACC | CTTCAAGCAT | TGAACAAATT | TGAACGGTTT | TGAACTATGC | 8640 |
| CCGGTTATCC | GCACTGCCGC | ACAAGCCAAG | GCCTGGCTTG | AACATCAAGG | TAAATCGGTT | 8700 |
| CAACAGTTCG | CTCGTGATCA | CGGGGTCGAT | CCAGCCACCA | CTTATCAGGT | ATTGGCTGGC | 8760 |
| CGCAAGAAAG | GACGGCGCGG | CGAGGCGCAC | AAGGTGACCG | TATTGCTGGG | CATGAAAGAC | 8820 |
| GGCGTCATCC | TGGCCGAACC | CGAGGGTCCC | GACCAGACGC | CGCCTGATC | TTCGAATGCC | 8880 |
| ATCATCCTGC | CGGGAAGAAT | CAACTGGCGG | CTACGCCTCC | ACGGCGCTGC | TTCGCTCCAT | 8940 |
| CCGCAGAAAA | CACTCGTCTT | CCCCGACCAC | TTTCAGCCCC | ATCCGCCCAT | AAAGCGCCTG | 9000 |
| CGCCGGATTG | TCCTTGAACA | CCGTCAGCCG | CAGCAGCCCA | CGCCGCTCGT | CATGCGCCAT | 9060 |
| CGCACGCACC | TGTTCGATGG | TCCAGGCCCC | GACGCCTTGC | CCGCGCGACG | CCTCGAGCAC | 9120 |
| ATGCAATTCA | CGAATGTACA | AAGCCTTGGC | ATCGCGACTC | AGGCTGACGA | ACCCCAGCAC | 9180 |

| | | | | | |
|---|---|---|---|---|---|
|CCTGGCGCCC|TGGCAGATCA|ACAGGTTCTG|CCGACCGGCC|CAGGCCACAT|CGAAGGCCTC|9240|
|ATCCAGCCAC|AACAGGTCGT|GACGAATGTG|ATAACCCAGC|ATGGTGCTGC|GGGTCAGGTC|9300|
|GCGGGCGAAC|ACCAGATCCT|CGTGGCTGCC|GGCCGGACGT|AGCTGCAGGC|CGTTCAAGGC|9360|
|GCGTCAACCG|GCAATGACTG|GCCACTCCAG|CGCCCGGCAT|TGCGCCTGGC|AATCAGCAGT|9420|
|TCGTCGCCTG|TACCGGCCGA|AGCCATGATC|AGCCCGCCGC|CGGCGCCCCA|GATCGCGCTA|9480|
|CGCCCCGCCG|ACACCCAGCC|CCCGGTCGGC|CGCCGTGGT|TGGCCATCAG|CACCAGCATT|9540|
|GCGTGCTCGG|CGGCATACCC|CTGCAACAAG|GCACTGTCCG|GGCATAGCC|TGTTTCGCCG|9600|
|ATCAAAACGC|CAGCGGCATA|GATGCCGGCA|CCGGAGTGCG|CCGCCGCACG|CGCGTGGCTG|9660|
|GCCTGGGAGA|AGTCGGCGCA|CACCGCCAGG|GCCACCTGGT|CTTCGGCGAA|CCTCAGGTTC|9720|
|GCGCCACCGG|TGCCGGGGCT|GAATACCCGC|TCCTCGCCAG|CATGCAGATG|CTGCTTGCTG|9780|
|TACACCGCCA|GCGAACCATC|GGCGGCCAGC|ACCAGGGCGC|CGATCAACAG|CGGCCCCTCG|9840|
|ACCGACAGGC|GGACGGGCAT|GCCCACCACC|GCTGTTACGC|CCCGCTCCCG|GGCCAGGTCG|9900|
|CGCAACGGTT|GCAACAGCGG|GCTCTGCGG|AGTATCGCCA|GCTCGGCCGC|CAGCGCGGGC|9960|
|TCATAACCGG|TCAGGGACAG|CTCGGGAAAT|ACCAGCAATT|GCACGCCCTG|CTCCGCCGCG|10020|
|ACGCGGATAA|AGGCCTGGTG|CCGGGCGATA|TTGCCCGGCA|GGTCTCCGGC|AACGGAAATC|10080|
|GACTGGGCGG|CGGCAAGGGT|CAGCATGGTC|ATGGTTCAAC|CTGAATCGGC|ATTCGGGAGG|10140|
|GCGTGGCGAG|TGTGTCATAA|AAAACTCAAA|GCGCTTCACT|CATAGACAGC|GACTGAAAAC|10200|
|GCAATAGGAT|TTTCTGATTG|AACCGCGCCC|CCGGCCTCTA|GTAAGCTCGG|CCCACTTCAC|10260|
|GGAGAAACAG|CATGTCGTCC|CTCACCCTTA|CCATGCATCG|TCACACTGCC|AGCGCCGCGC|10320|
|GCTCCGGTGC|GGCTGCCTGG|GTGAAAAACG|CCTGCGCTCC|GGCGGGCTTT|TATTTTGGGT|10380|
|ATTGGTTTAG|CCACTGGCGC|GCCTGATACC|CAAACGGCGC|CCACTTGAAC|GGGTCGCCTA|10440|
|CCAGAGAAAA|TCTCACCCCC|GGTCGGCCTC|CCGACCGGGG|GTTTGTTTT|TCTGGGCCGA|10500|
|AGATTTTTAA|CCGCGACTTC|TTAAGCAACA|CACCGAACTT|ACCGAGGATT|GAACCATGAA|10560|
|CTACGCCACC|TATTACCGTT|ACGACACTTG|CACCACCTGG|CGATTTAGCA|GCCTCCGTTC|10620|
|GGGACAGCCT|GCCGCCTCCG|ATCGGTCACC|TACTGGTGGC|AAACATACCT|GCACAGCCAA|10680|
|TCCGGCCAAT|TGTCGAACAC|CCCAGTAGGG|CCGCGCGCGG|GAAATCACCC|GCCGCCTGCC|10740|
|CAGGAAGCCT|TGAACATGAA|TTC| | | |10763|

( 2 ) INFORMATION FOR SEQ ID NO:2:

( i ) SEQUENCE CHARACTERISTICS:
        ( A ) LENGTH: 642 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudomonas fluorescens
        ( B ) STRAIN: CGA267356 (aka MOCG134 and aka BL915)

( i x ) FEATURE:
        ( A ) NAME/KEY: CDS
        ( B ) LOCATION: 1..639
        ( D ) OTHER INFORMATION: /transl_except=(pos: 1 .. 3, aa: Met ( x i ) SEQUENCE DESCRIPTION: SEQ ID NO:2:

| | | | | | | | | | | | | | | | | |
|---|---|---|---|---|---|---|---|---|---|---|---|---|---|---|---|---|
| TTG | ATT | AGG | GTG | CTA | GTA | GTC | GAT | GAC | CAT | GAT | CTC | GTT | CGT | ACA | GGT | 48 |
| Met | Ile | Arg | Val | Leu | Val | Val | Asp | Asp | His | Asp | Leu | Val | Arg | Thr | Gly | |
| 1 | | | | 5 | | | | | 10 | | | | | 15 | | |
| ATT | ACA | CGA | ATG | CTG | GCT | GAC | ATC | GAT | GGC | CTG | CAA | GTG | GTC | GGC | CAG | 96 |
| Ile | Thr | Arg | Met | Leu | Ala | Asp | Ile | Asp | Gly | Leu | Gln | Val | Val | Gly | Gln | |
| | | | 20 | | | | | 25 | | | | | 30 | | | |
| GCC | GAG | TCA | GGG | GAG | GAA | TCC | CTG | CTC | AAG | GCC | CGG | GAG | TTG | AAA | CCC | 144 |
| Ala | Glu | Ser | Gly | Glu | Glu | Ser | Leu | Leu | Lys | Ala | Arg | Glu | Leu | Lys | Pro | |
| | | 35 | | | | | 40 | | | | | 45 | | | | |
| GAT | GTG | GTC | CTC | ATG | GAC | GTC | AAG | ATG | CCC | GGG | ATC | GGC | GGT | CTT | GAA | 192 |
| Asp | Val | Val | Leu | Met | Asp | Val | Lys | Met | Pro | Gly | Ile | Gly | Gly | Leu | Glu | |
| | 50 | | | | | 55 | | | | | 60 | | | | | |
| GCC | ACG | CGC | AAA | TTG | TTG | CGC | AGT | CAC | CCG | GAT | ATC | AAA | GTC | GTG | GCC | 240 |
| Ala | Thr | Arg | Lys | Leu | Leu | Arg | Ser | His | Pro | Asp | Ile | Lys | Val | Val | Ala | |
| 65 | | | | | 70 | | | | | 75 | | | | | 80 | |
| GTC | ACC | GTG | TGT | GAA | GAA | GAT | CCG | TTC | CCG | ACC | CGC | TTG | CTG | CAA | GCC | 288 |
| Val | Thr | Val | Cys | Glu | Glu | Asp | Pro | Phe | Pro | Thr | Arg | Leu | Leu | Gln | Ala | |
| | | | | 85 | | | | | 90 | | | | | 95 | | |
| GGC | GCG | GCG | GGT | TAC | CTG | ACC | AAG | GGG | GCG | GGC | CTC | AAT | GAA | ATG | GTG | 336 |
| Gly | Ala | Ala | Gly | Tyr | Leu | Thr | Lys | Gly | Ala | Gly | Leu | Asn | Glu | Met | Val | |
| | | | 100 | | | | | 105 | | | | | 110 | | | |
| CAG | GCC | ATT | CGC | CTG | GTG | TTT | GCC | GGC | CAG | CGT | TAC | ATC | AGC | CCG | CAA | 384 |
| Gln | Ala | Ile | Arg | Leu | Val | Phe | Ala | Gly | Gln | Arg | Tyr | Ile | Ser | Pro | Gln | |
| | | 115 | | | | | 120 | | | | | 125 | | | | |
| ATT | GCC | CAG | CAG | TTG | GTG | TTC | AAG | TCA | TTC | CAG | CCT | TCC | AGT | GAT | TCA | 432 |
| Ile | Ala | Gln | Gln | Leu | Val | Phe | Lys | Ser | Phe | Gln | Pro | Ser | Ser | Asp | Ser | |
| | 130 | | | | | 135 | | | | | 140 | | | | | |
| CCG | TTC | GAT | GCT | TTG | TCC | GAG | CGG | GAA | ATC | CAG | ATC | GCG | CTG | ATG | ATT | 480 |
| Pro | Phe | Asp | Ala | Leu | Ser | Glu | Arg | Glu | Ile | Gln | Ile | Ala | Leu | Met | Ile | |
| 145 | | | | | 150 | | | | | 155 | | | | | 160 | |
| GTC | GGC | TGC | CAG | AAA | GTG | CAG | ATC | ATC | TCC | GAC | AAG | CTG | TGC | CTG | TCT | 528 |
| Val | Gly | Cys | Gln | Lys | Val | Gln | Ile | Ile | Ser | Asp | Lys | Leu | Cys | Leu | Ser | |
| | | | | 165 | | | | | 170 | | | | | 175 | | |
| CCG | AAA | ACC | GTT | AAT | ACC | TAC | CGT | TAC | CGC | ATC | TTC | GAA | AAG | CTC | TCG | 576 |
| Pro | Lys | Thr | Val | Asn | Thr | Tyr | Arg | Tyr | Arg | Ile | Phe | Glu | Lys | Leu | Ser | |
| | | | 180 | | | | | 185 | | | | | 190 | | | |
| ATC | AGC | AGC | GAT | GTT | GAA | CTG | ACA | TTG | CTG | GCG | GTT | CGC | CAC | GGC | ATG | 624 |
| Ile | Ser | Ser | Asp | Val | Glu | Leu | Thr | Leu | Leu | Ala | Val | Arg | His | Gly | Met | |
| | | 195 | | | | | 200 | | | | | 205 | | | | |
| GTC | GAT | GCC | AGT | GCC | TGA | | | | | | | | | | | 642 |
| Val | Asp | Ala | Ser | Ala | | | | | | | | | | | | |
| | 210 | | | | | | | | | | | | | | | |

( 2 ) INFORMATION FOR SEQ ID NO:3:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Ile | Arg | Val | Leu | Val | Val | Asp | Asp | His | Asp | Leu | Val | Arg | Thr | Gly |
| 1 | | | | 5 | | | | | 10 | | | | | 15 | |
| Ile | Thr | Arg | Met | Leu | Ala | Asp | Ile | Asp | Gly | Leu | Gln | Val | Val | Gly | Gln |
| | | | 20 | | | | | 25 | | | | | 30 | | |
| Ala | Glu | Ser | Gly | Glu | Glu | Ser | Leu | Leu | Lys | Ala | Arg | Glu | Leu | Lys | Pro |
| | | 35 | | | | | 40 | | | | | 45 | | | |
| Asp | Val | Val | Leu | Met | Asp | Val | Lys | Met | Pro | Gly | Ile | Gly | Gly | Leu | Glu |
| | 50 | | | | | 55 | | | | | 60 | | | | |

```
Ala Thr Arg Lys Leu Leu Arg Ser His Pro Asp Ile Lys Val Val Ala
65              70              75              80

Val Thr Val Cys Glu Glu Asp Pro Phe Pro Thr Arg Leu Leu Gln Ala
                85              90              95

Gly Ala Ala Gly Tyr Leu Thr Lys Gly Ala Gly Leu Asn Glu Met Val
            100             105             110

Gln Ala Ile Arg Leu Val Phe Ala Gly Gln Arg Tyr Ile Ser Pro Gln
        115             120             125

Ile Ala Gln Gln Leu Val Phe Lys Ser Phe Gln Pro Ser Ser Asp Ser
    130             135             140

Pro Phe Asp Ala Leu Ser Glu Arg Glu Ile Gln Ile Ala Leu Met Ile
145             150             155             160

Val Gly Cys Gln Lys Val Gln Ile Ile Ser Asp Lys Leu Cys Leu Ser
            165             170             175

Pro Lys Thr Val Asn Thr Tyr Arg Tyr Arg Ile Phe Glu Lys Leu Ser
            180             185             190

Ile Ser Ser Asp Val Glu Leu Thr Leu Leu Ala Val Arg His Gly Met
        195             200             205

Val Asp Ala Ser Ala
210
```

( 2 ) INFORMATION FOR SEQ ID NO:4:

( i ) SEQUENCE CHARACTERISTICS:
( A ) LENGTH: 642 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Pseudomonas fluorescens
( B ) STRAIN: CGA267356 (aka MOCG134 and aka BL915)

( i x ) FEATURE:
( A ) NAME/KEY: misc_feature
( B ) LOCATION: 1..3
( D ) OTHER INFORMATION: /note="TTG initiation codon in
native sequence modified to ATG initiation codon."

( i x ) FEATURE:
( A ) NAME/KEY: CDS
( B ) LOCATION: 1..639

( x i ) SEQUENCE DESCRIPTION: SEQ ID NO:4:

```
ATG ATT AGG GTG CTA GTA GTC GAT GAC CAT GAT CTC GTT CGT ACA GGT     48
Met Ile Arg Val Leu Val Val Asp Asp His Asp Leu Val Arg Thr Gly
1               5               10              15

ATT ACA CGA ATG CTG GCT GAC ATC GAT GGC CTG CAA GTG GTC GGC CAG     96
Ile Thr Arg Met Leu Ala Asp Ile Asp Gly Leu Gln Val Val Gly Gln
            20              25              30

GCC GAG TCA GGG GAG GAA TCC CTG CTC AAG GCC CGG GAG TTG AAA CCC    144
Ala Glu Ser Gly Glu Glu Ser Leu Leu Lys Ala Arg Glu Leu Lys Pro
        35              40              45

GAT GTG GTC CTC ATG GAC GTC AAG ATG CCC GGG ATC GGC GGT CTT GAA    192
Asp Val Val Leu Met Asp Val Lys Met Pro Gly Ile Gly Gly Leu Glu
    50              55              60

GCC ACG CGC AAA TTG TTG CGC AGT CAC CCG GAT ATC AAA GTC GTG GCC    240
Ala Thr Arg Lys Leu Leu Arg Ser His Pro Asp Ile Lys Val Val Ala
65              70              75              80
```

| | | | | | | | | | | | | | | | | |
|---|---|---|---|---|---|---|---|---|---|---|---|---|---|---|---|---|
|GTC|ACC|GTG|TGT|GAA|GAA|GAT|CCG|TTC|CCG|ACC|CGC|TTG|CTG|CAA|GCC|288|
|Val|Thr|Val|Cys|Glu 85|Glu|Asp|Pro|Phe|Pro 90|Thr|Arg|Leu|Leu|Gln 95|Ala| |
|GGC|GCG|GCG|GGT|TAC|CTG|ACC|AAG|GGG|GCG|GGC|CTC|AAT|GAA|ATG|GTG|336|
|Gly|Ala|Ala|Gly 100|Tyr|Leu|Thr|Lys|Gly 105|Ala|Gly|Leu|Asn|Glu 110|Met|Val| |
|CAG|GCC|ATT|CGC|CTG|GTG|TTT|GCC|GGC|CAG|CGT|TAC|ATC|AGC|CCG|CAA|384|
|Gln|Ala|Ile 115|Arg|Leu|Val|Phe|Ala|Gly 120|Gln|Arg|Tyr|Ile|Ser 125|Pro|Gln| |
|ATT|GCC|CAG|CAG|TTG|GTG|TTC|AAG|TCA|TTC|CAG|CCT|TCC|AGT|GAT|TCA|432|
|Ile|Ala 130|Gln|Gln|Leu|Val|Phe 135|Lys|Ser|Phe|Gln|Pro 140|Ser|Ser|Asp|Ser| |
|CCG|TTC|GAT|GCT|TTG|TCC|GAG|CGG|GAA|ATC|CAG|ATC|GCG|CTG|ATG|ATT|480|
|Pro 145|Phe|Asp|Ala|Leu|Ser 150|Glu|Arg|Glu|Ile|Gln 155|Ile|Ala|Leu|Met|Ile 160| |
|GTC|GGC|TGC|CAG|AAA|GTG|CAG|ATC|ATC|TCC|GAC|AAG|CTG|TGC|CTG|TCT|528|
|Val|Gly|Cys|Gln|Lys 165|Val|Gln|Ile|Ile|Ser 170|Asp|Lys|Leu|Cys 175|Leu|Ser| |
|CCG|AAA|ACC|GTT|AAT|ACC|TAC|CGT|TAC|CGC|ATC|TTC|GAA|AAG|CTC|TCG|576|
|Pro|Lys|Thr|Val 180|Asn|Thr|Tyr|Arg|Tyr 185|Arg|Ile|Phe|Glu|Lys 190|Leu|Ser| |
|ATC|AGC|AGC|GAT|GTT|GAA|CTG|ACA|TTG|CTG|GCG|GTT|CGC|CAC|GGC|ATG|624|
|Ile|Ser|Ser 195|Asp|Val|Glu|Leu|Thr 200|Leu|Leu|Ala|Val|Arg 205|His|Gly|Met| |
|GTC|GAT|GCC|AGT|GCC|TGA| | | | | | | | | | |642|
|Val|Asp|Ala|Ser|Ala 210| | | | | | | | | | | | |

( 2 ) INFORMATION FOR SEQ ID NO:5:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
|Met 1|Ile|Arg|Val|Leu 5|Val|Val|Asp|Asp|His 10|Asp|Leu|Val|Arg|Thr 15|Gly|
|Ile|Thr|Arg|Met 20|Leu|Ala|Asp|Ile|Asp 25|Gly|Leu|Gln|Val|Val 30|Gly|Gln|
|Ala|Glu|Ser 35|Gly|Glu|Glu|Ser|Leu 40|Leu|Lys|Ala|Arg|Glu 45|Leu|Lys|Pro|
|Asp|Val 50|Leu|Met|Asp|Val|Lys 55|Met|Pro|Gly|Ile|Gly 60|Gly|Leu|Glu| |
|Ala|Thr|Arg|Lys|Leu|Leu 70|Arg|Ser|His|Pro|Asp 75|Ile|Lys|Val|Val|Ala|
|65| | | | | | | | | | | | | | |80|
|Val|Thr|Val|Cys|Glu 85|Glu|Asp|Pro|Phe|Pro 90|Thr|Arg|Leu|Leu|Gln 95|Ala|
|Gly|Ala|Ala|Gly 100|Tyr|Leu|Thr|Lys|Gly 105|Ala|Gly|Leu|Asn|Glu 110|Met|Val|
|Gln|Ala|Ile 115|Arg|Leu|Val|Phe|Ala 120|Gly|Gln|Arg|Tyr|Ile 125|Ser|Pro|Gln|
|Ile|Ala 130|Gln|Gln|Leu|Val|Phe 135|Lys|Ser|Phe|Gln|Pro 140|Ser|Ser|Asp|Ser|
|Pro 145|Phe|Asp|Ala|Leu|Ser 150|Glu|Arg|Glu|Ile|Gln 155|Ile|Ala|Leu|Met|Ile 160|
|Val|Gly|Cys|Gln|Lys|Val|Gln|Ile|Ile|Ser|Asp|Lys|Leu|Cys|Leu|Ser|

|     |     |     |     |     |     | 165 |     |     |     |     |     | 170 |     |     |     |     |     | 175 |     |
| --- | --- | --- | --- | --- | --- | --- | --- | --- | --- | --- | --- | --- | --- | --- | --- | --- | --- | --- | --- |
| Pro | Lys | Thr | Val | Asn | Thr | Tyr | Arg | Tyr | Arg | Ile | Phe | Glu | Lys | Leu | Ser |
|     |     |     | 180 |     |     |     |     | 185 |     |     |     |     | 190 |     |     |
| Ile | Ser | Ser | Asp | Val | Glu | Leu | Thr | Leu | Leu | Ala | Val | Arg | His | Gly | Met |
|     |     | 195 |     |     |     |     | 200 |     |     |     |     | 205 |     |     |     |
| Val | Asp | Ala | Ser | Ala |
|     |     | 210 |     |     |

( 2 ) INFORMATION FOR SEQ ID NO:6:

( i ) SEQUENCE CHARACTERISTICS:
        ( A ) LENGTH: 7001 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudomonas fluorescens
        ( B ) STRAIN: CGA267356 (aka MOCG134 and aka BL915)

( v i i ) IMMEDIATE SOURCE:
        ( B ) CLONE: pCIB169

( i x ) FEATURE:
        ( A ) NAME/KEY: misc_feature
        ( B ) LOCATION: 423..2036
        ( D ) OTHER INFORMATION: /product="PrnA"
            / note="ORF1"

( i x ) FEATURE:
        ( A ) NAME/KEY: misc_feature
        ( B ) LOCATION: 2039..3121
        ( D ) OTHER INFORMATION: /product="PrnB"
            / note="ORF2"

( i x ) FEATURE:
        ( A ) NAME/KEY: misc_feature
        ( B ) LOCATION: 3167..4867
        ( D ) OTHER INFORMATION: /product="PrnC"
            / note="ORF3"

( i x ) FEATURE:
        ( A ) NAME/KEY: misc_feature
        ( B ) LOCATION: 4895..5983
        ( D ) OTHER INFORMATION: /product="PrnD"
            / note="ORF4"

( x i ) SEQUENCE DESCRIPTION: SEQ ID NO:6:

```
GAATTCCGAC  AACGCCGAAG  AAGCGCGGAA  CCGCTGAAAG  AGGAGCAGGA  ACTGGAGCAA      60

ACGCTGTCCC  AGGTGATCGA  CAGCCTGCCA  CTGCGCATCG  AGGGCCGATG  AACAGCATTG     120

GCAAAAGCTG  GCGGTGCGCA  GTGCGCGAGT  GATCCGATCA  TTTTTGATCG  GCTCGCCTCT     180

TCAAAATCGG  CGGTGGATGA  AGTCGACGGC  GGACTGATCA  GGCGCAAAAG  AACATGCGCC     240

AAAACCTTCT  TTTATAGCGA  ATACCTTTGC  ACTTCAGAAT  GTTAATTCGG  AAACGGAATT     300

TGCATCGCTT  TTCCGGCAGT  CTAGAGTCTC  TAACAGCACA  TTGATGTGCC  TCTTGCATGG     360

ATGCACGAAG  ACTGGCGGCC  TCCCCTCGTC  ACAGGCGGCC  CGCCTTTGAA  ACAAGGAGTG     420

TTATGAACAA  GCCGATCAAG  AATATCGTCA  TCGTGGGCGG  CGGTACTGCG  GGCTGGATGG     480

CCGCCTCGTA  CCTCGTCCGG  GCCCTCCAAC  AGCAGGCGAA  CATTACGCTC  ATCGAATCTG     540

CGGCGATCCC  TCGGATCGGC  GTGGGCGAAG  CGACCATCCC  AAGTTTGCAG  AAGGTGTTCT     600

TCGATTTCCT  CGGGATACCG  GAGCGGGAAT  GGATGCCCCA  AGTGAACGGC  GCGTTCAAGG     660
```

```
CCGCGATCAA GTTCGTGAAT TGGAGAAAGT CTCCCGACCC CTCGCGCGAC GATCACTTCT      720
ACCATTTGTT CGGCAACGTG CCGAACTGCG ACGGCGTGCC GCTTACCCAC TACTGGCTGC      780
GCAAGCGCGA ACAGGGCTTC CAGCAGCCGA TGGAGTACGC GTGCTACCCG CAGCCCGGGG      840
CACTCGACGG CAAGCTGGCA CCGTGCCTGT CCGACGGCAC CCGCCAGATG TCCCACGCGT      900
GGCACTTCGA CGCGCACCTG GTGGCCGACT TCTTGAAGCG CTGGGCCGTC GAGCGCGGGG      960
TGAACCGCGT GGTCGATGAG GTGGTGGACG TTCGCCTGAA CAACCGCGGC TACATCTCCA     1020
ACCTGCTCAC CAAGGAGGGG CGGACGCTGG AGGCGGACCT GTTCATCGAC TGCTCCGGCA     1080
TGCGGGGGCT CCTGATCAAT CAGGCGCTGA AGGAACCCTT CATCGACATG TCCGACTACC     1140
TGCTGTGCGA CAGCGCGGTC GCCAGCGCCG TGCCCAACGA CGACGCGCGC GATGGGGTCG     1200
AGCCGTACAC CTCCTCGATC GCCATGAACT CGGGATGGAC CTGGAAGATT CCGATGCTGG     1260
GCCGGTTCGG CAGCGGCTAC GTCTTCTCGA GCCATTTCAC CTCGCGCGAC CAGGCCACCG     1320
CCGACTTCCT CAAACTCTGG GGCCTCTCGG ACAATCAGCC GCTCAACCAG ATCAAGTTCC     1380
GGGTCGGGCG CAACAAGCGG GCGTGGGTCA ACAACTGCGT CTCGATCGGG CTGTCGTCGT     1440
GCTTTCTGGA GCCCCTGGAA TCGACGGGGA TCTACTTCAT CTACGCGGCG CTTTACCAGC     1500
TCGTGAAGCA CTTCCCCGAC ACCTCGTTCG ACCCGCGGCT GAGCGACGCT TTCAACGCCG     1560
AGATCGTCCA CATGTTCGAC GACTGCCGGG ATTTCGTCCA AGCGCACTAT TTCACCACGT     1620
CGCGCGATGA CACGCCGTTC TGGCTCGCGA ACCGGCACGA CCTGCGGCTC TCGGACGCCA     1680
TCAAAGAGAA GGTTCAGCGC TACAAGGCGG GGCTGCCGCT GACCACCACG TCGTTCGACG     1740
ATTCCACGTA CTACGAGACC TTCGACTACG AATTCAAGAA TTTCTGGTTG AACGGCAACT     1800
ACTACTGCAT CTTTGCCGGC TTGGGCATGC TGCCCGACCG GTCGCTGCCG CTGTTGCAGC     1860
ACCGACCGGA GTCGATCGAG AAAGCCGAGG CGATGTTCGC CAGCATCCGG CGCGAGGCCG     1920
AGCGTCTGCG CACCAGCCTG CCGACAAACT ACGACTACCT GCGGTCGCTG CGTGACGGCG     1980
ACGCGGGGCT GTCGCGCGGC CAGCGTGGGC CGAAGCTCGC AGCGCAGGAA AGCCTGTAGT     2040
GGAACGCACC TTGGACCGGG TAGGCGTATT CGCGGCCACC CACGCTGCCG TGGCGGCCTG     2100
CGATCCGCTG CAGGCGCGCG CGCTCGTTCT GCAACTGCCG GGCCTGAACC GTAACAAGGA     2160
CGTGCCCGGT ATCGTCGGCC TGCTGCGCGA GTTCCTTCCG GTGCGCGGCC TGCCCTGCGG     2220
CTGGGGTTTC GTCGAAGCCG CCGCCGCGAT GCGGGACATC GGGTTCTTCC TGGGGTCGCT     2280
CAAGCGCCAC GGACATGAGC CCGCGGAGGT GGTGCCCGGG CTTGAGCCGG TGCTGCTCGA     2340
CCTGGCACGC GCGACCAACC TGCCGCCGCG CGAGACGCTC CTGCATGTGA CGGTCTGGAA     2400
CCCCACGGCG GCCGACGCGC AGCGCAGCTA CACCGGGCTG CCCGACGAAG CGCACCTGCT     2460
CGAGAGCGTG CGCATCTCGA TGGCGGCCCT CGAGGCGGCC ATCGCGTTGA CCGTCGAGCT     2520
GTTCGATGTG TCCCTGCGGT CGCCCGAGTT CGCGCAAAGG TGCGACGAGC TGGAAGCCTA     2580
TCTGCAGAAA ATGGTCGAAT CGATCGTCTA CGCGTACCGC TTCATCTCGC CGCAGGTCTT     2640
CTACGATGAG CTGCGCCCCT TCTACGAACC GATTCGAGTC GGGGGCCAGA GCTACCTCGG     2700
CCCCGGTGCC GTAGAGATGC CCCTCTTCGT GCTGGAGCAC GTCCTCTGGG GCTCGCAATC     2760
GGACGACCAA ACTTATCGAG AATTCAAAGA GACGTACCTG CCCTATGTGC TTCCCGCGTA     2820
CAGGGCGGTC TACGCTCGGT TCTCCGGGGA GCCGGCGCTC ATCGACCGCG CGCTCGACGA     2880
GGCGCGAGCG GTCGGTACGC GGGACGAGCA CGTCCGGGCT GGGCTGACAG CCCTCGAGCG     2940
GGTCTTCAAG GTCCTGCTGC GCTTCCGGGC GCCTCACCTC AAATTGGCGG AGCGGGCGTA     3000
CGAAGTCGGG CAAAGCGGCC CCGAAATCGG CAGCGGGGGG TACGCGCCCA GCATGCTCGG     3060
```

```
TGAGCTGCTC ACGCTGACGT ATGCCGCGCG GTCCCGCGTC CGCGCCGCGC TCGACGAATC     3120
CTGATGCGCG CGACCCAGTG TTATCTCACA AGGAGAGTTT GCCCCCATGA CTCAGAAGAG     3180
CCCCGCGAAC GAACACGATA GCAATCACTT CGACGTAATC ATCCTCGGCT CGGGCATGTC     3240
CGGCACCCAG ATGGGGGCCA TCTTGGCCAA ACAACAGTTT CGCGTGCTGA TCATCGAGGA     3300
GTCGTCGCAC CCGCGGTTCA CGATCGGCGA ATCGTCGATC CCCGAGACGT CTCTTATGAA     3360
CCGCATCATC GCTGATCGCT ACGGCATTCC GGAGCTCGAC CACATCACGT CGTTTTATTC     3420
GACGCAACGT TACGTCGCGT CGAGCACGGG CATTAAGCGC AACTTCGGCT TCGTGTTCCA     3480
CAAGCCCGGC CAGGAGCACG ACCCGAAGGA GTTCACCCAG TGCGTCATTC CCGAGCTGCC     3540
GTGGGGGCCG GAGAGCCATT ATTACCGGCA AGACGTCGAC GCCTACTTGT TGCAAGCCGC     3600
CATTAAATAC GGCTGCAAGG TCCACCAGAA AACTACCGTG ACCGAATACC ACGCCGATAA     3660
AGACGGCGTC GCGGTGACCA CCGCCCAGGG CGAACGGTTC ACCGGCCGGT ACATGATCGA     3720
CTGCGGAGGA CCTCGCGCGC CGCTCGCGAC CAAGTTCAAG CTCCGCGAAG AACCGTGTCG     3780
CTTCAAGACG CACTCGCGCA GCCTCTACAC GCACATGCTC GGGGTCAAGC CGTTCGACGA     3840
CATCTTCAAG GTCAAGGGGC AGCGCTGGCG CTGGCACGAG GGGACCTTGC ACCACATGTT     3900
CGAGGGCGGC TGGCTCTGGG TGATTCCGTT CAACAACCAC CCGCGGTCGA CCAACAACCT     3960
GGTGAGCGTC GGCCTGCAGC TCGACCCGCG TGTCTACCCG AAAACCGACA TCTCCGCACA     4020
GCAGGAATTC GATGAGTTCC TCGCGCGGTT CCCGAGCATC GGGGCTCAGT TCCGGGACGC     4080
CGTGCCGGTG CGCGACTGGG TCAAGACCGA CCGCCTGCAA TTCTCGTCGA ACGCCTGCGT     4140
CGGCGACCGC TACTGCCTGA TGCTGCACGC GAACGGCTTC ATCGACCCGC TCTTCTCCCG     4200
GGGGCTGGAA AACACCGCGG TGACCATCCA CGCGCTCGCG GCGCGCCTCA TCAAGGCGCT     4260
GCGCGACGAC GACTTCTCCC CCGAGCGCTT CGAGTACATC GAGCGCCTGC AGCAAAAGCT     4320
TTTGGACCAC AACGACGACT TCGTCAGCTG CTGCTACACG GCGTTCTCGG ACTTCCGCCT     4380
ATGGGACGCG TTCCACAGGC TGTGGGCGGT CGGCACCATC CTCGGGCAGT TCCGGCTCGT     4440
GCAGGCCCAC GCGAGGTTCC GCGCGTCGCG CAACGAGGGC GACCTCGATC ACCTCGACAA     4500
CGACCCTCCG TATCTCGGAT ACCTGTGCGC GGACATGGAG GAGTACTACC AGTTGTTCAA     4560
CGACGCCAAA GCCGAGGTCG AGGCCGTGAG TGCCGGGCGC AAGCCGGCCG ATGAGGCCGC     4620
GGCGCGGATT CACGCCCTCA TTGACGAACG AGACTTCGCC AAGCCGATGT TCGGCTTCGG     4680
GTACTGCATC ACCGGGGACA AGCCGCAGCT CAACAACTCG AAGTACAGCC TGCTGCCGGC     4740
GATGCGGCTG ATGTACTGGA CGCAAACCCG CGCGCCGGCA GAGGTGAAAA AGTACTTCGA     4800
CTACAACCCG ATGTTCGCGC TGCTCAAGGC GTACATCACG ACCCGCATCG GCCTGGCGCT     4860
GAAGAAGTAG CCGCTCGACG ACGACATAAA AACGATGAAC GACATTCAAT TGGATCAAGC     4920
GAGCGTCAAG AAGCGTCCCT CGGGCGCGTA CGACGCAACC ACGCGCCTGG CCGCGAGCTG     4980
GTACGTCGCG ATGCGCTCCA ACGAGCTCAA GGACAAGCCG ACCGAGTTGA CGCTCTTCGG     5040
CCGTCCGTGC GTGGCGTGGC GCGGAGCCAC GGGGCGGGCC GTGGTGATGG ACCGCCACTG     5100
CTCGCACCTG GGCGCGAACC TGGCTGACGG GCGGATCAAG GACGGGTGCA TCCAGTGCCC     5160
GTTTCACCAC TGGCGGTACG ACGAACAGGG CCAGTGCGTT CACATCCCCG GCCATAACCA     5220
GGCGGTGCGC CAGCTGGAGC CGGTGCCGCG CGGGGCGCGT CAGCCGACGT TGGTCACCGC     5280
CGAGCGATAC GGCTACGTGT GGGTCTGGTA CGGCTCCCCG CTGCCGCTGC ACCCGCTGCC     5340
CGAAATCTCC GCGGCCGATG TCGACAACGG CGACTTTATG CACCTGCACT TCGCGTTCGA     5400
GACGACCACG GCGGTCTTGC GGATCGTCGA GAACTTCTAC GACGCGCAGC ACGCAACCCC     5460
```

-continued

```
GGTGCACGCA CTCCCGATCT CGGCCTTCGA ACTCAAGCTC TTCGACGATT GGCGCCAGTG   5520
GCCGGAGGTT GAGTCGCTGG CCCTGGCGGG CGCGTGGTTC GGTGCCGGGA TCGACTTCAC   5580
CGTGGACCGG TACTTCGGCC CCCTCGGCAT GCTGTCACGC GCGCTCGGCC TGAACATGTC   5640
GCAGATGAAC CTGCACTTCG ATGGCTACCC CGGCGGGTGC GTCATGACCG TCGCCCTGGA   5700
CGGAGACGTC AAATACAAGC TGCTCCAGTG TGTGACGCCG GTGAGCGAAG GCAAGAACGT   5760
CATGCACATG CTCATCTCGA TCAAGAAGGT GGGCGGCATC CTGCGCCGCG CGACCGACTT   5820
CGTGCTGTTC GGGCTGCAGA CCAGGCAGGC CGCGGGGTAC GACGTCAAAA TCTGGAACGG   5880
AATGAAGCCG GACGGCGGCG GCGCGTACAG CAAGTACGAC AAGCTCGTGC TCAAGTACCG   5940
GGCGTTCTAT CGAGGCTGGG TCGACCGCGT CGCAAGTGAG CGGTGATGCG TGAAGCCGAG   6000
CCGCTCTCGA CCGCGTCGCT GCGCCAGGCG CTCGCGAACC TGGCGAGCGG CGTGACGATC   6060
ACGGCCTACG GCGCGCCGGG CCCGCTTGGG CTCGCGGCCA CCAGCTTCGT GTCGGAGTCG   6120
CTCTTTGCGA GGTATTCATG ACTATCTGGC TGTTGCAACT CGTGCTGGTG ATCGCGCTCT   6180
GCAACGTCTG CGGCCGCATT GCCGAACGGC TCGGCCAGTG CGCGGTCATC GGCGAGATCG   6240
CGGCCGGTTT GCTGTTGGGG CCGTCGCTGT TCGGCGTGAT CGCACCGAGT TTCTACGACC   6300
TGTTGTTCGG CCCCCAGGTG CTGTCAGCGA TGGCGCAAGT CAGCGAAGTC GGCCTGGTAC   6360
TGCTGATGTT CCAGGTCGGC CTGCATATGG AGTTGGGCGA GACGCTGCGC GACAAGCGCT   6420
GGCGCATGCC CGTCGCGATC GCAGCGGGCG GGCTCGTCGC ACCGGCCGCG ATCGGCATGA   6480
TCGTCGCCAT CGTTTCGAAA GGCACGCTCG CCAGCGACGC GCCGGCGCTG CCCTATGTGC   6540
TCTTCTGCGG TGTCGCACTT GCGGTATCGG CGGTGCCGGT GATGGCGCGC ATCATCGACG   6600
ACCTGGAGCT CAGCGCCATG GTGGGCGCGC GGCACGCAAT GTCTGCCGCG ATGCTGACGG   6660
ATGCGCTCGG ATGGATGCTG CTTGCAACGA TTGCCTCGCT ATCGAGCGGG CCCGGCTGGG   6720
CATTTGCGCG CATGCTCGTC AGCCTGCTCG CGTATCTGGT GCTGTGCGCG CTGCTGGTGC   6780
GCTTCGTGGT TCGACCGACC CTTGCGCGGC TCGCGTCGAC CGCGCATGCG ACGCGCGACC   6840
GCTTGGCCGT GTTGTTCTGC TTCGTAATGT TGTCGGCACT CGCGACGTCG CTGATCGGAT   6900
TCCATAGCGC TTTTGGCGCA CTTGCCGCGG CGCTGTTCGT GCGCCGGGTG CCCGGCGTCG   6960
CGAAGGAGTG GCGCGACAAC GTCGAAGGTT TCGTCAAGCT T                       7001
```

(2) INFORMATION FOR SEQ ID NO:7:

(i) SEQUENCE CHARACTERISTICS:
        (A) LENGTH: 1097 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: pKK223-3

(ix) FEATURE:
        (A) NAME/KEY: misc_feature
        (B) LOCATION: 1
        (D) OTHER INFORMATION: /note="BssHII site"

(ix) FEATURE:
        (A) NAME/KEY: misc_feature
        (B) LOCATION: 7
        (D) OTHER INFORMATION: /note="BglII site"

(ix) FEATURE:
        (A) NAME/KEY: misc_feature
        (B) LOCATION: 265

(D) OTHER INFORMATION: /note="EcoRI site"

(ix) FEATURE:
  (A) NAME/KEY: misc_feature
  (B) LOCATION: 270
  (D) OTHER INFORMATION: /note="SmaI site"

(ix) FEATURE:
  (A) NAME/KEY: misc_feature
  (B) LOCATION: 275
  (D) OTHER INFORMATION: /note="BamHI site"

(ix) FEATURE:
  (A) NAME/KEY: misc_feature
  (B) LOCATION: 281
  (D) OTHER INFORMATION: /note="SalI site"

(ix) FEATURE:
  (A) NAME/KEY: misc_feature
  (B) LOCATION: 287
  (D) OTHER INFORMATION: /note="PstI site"

(ix) FEATURE:
  (A) NAME/KEY: misc_feature
  (B) LOCATION: 293
  (D) OTHER INFORMATION: /note="XbaI site"

(ix) FEATURE:
  (A) NAME/KEY: misc_feature
  (B) LOCATION: 299
  (D) OTHER INFORMATION: /note="XhoI site"

(ix) FEATURE:
  (A) NAME/KEY: misc_feature
  (B) LOCATION: 305
  (D) OTHER INFORMATION: /note="KpnI site"

(ix) FEATURE:
  (A) NAME/KEY: misc_feature
  (B) LOCATION: 311
  (D) OTHER INFORMATION: /note="NotI site"

(ix) FEATURE:
  (A) NAME/KEY: misc_feature
  (B) LOCATION: 319
  (D) OTHER INFORMATION: /note="HindIII site"

(ix) FEATURE:
  (A) NAME/KEY: misc_feature
  (B) LOCATION: 1086
  (D) OTHER INFORMATION: /note="BglI site"

(ix) FEATURE:
  (A) NAME/KEY: misc_feature
  (B) LOCATION: 1092
  (D) OTHER INFORMATION: /note="BssHII site"

(ix) FEATURE:
  (A) NAME/KEY: promoter
  (B) LOCATION: 185..264
  (D) OTHER INFORMATION: /standard_name="tac"

(ix) FEATURE:
  (A) NAME/KEY: terminator
  (B) LOCATION: 327..752
  (D) OTHER INFORMATION: /standard_name="rrnB"

(xi) SEQUENCE DESCRIPTION: SEQ ID NO:7:

| | | | | | |
|---|---|---|---|---|---|
| GCGCGCAGAT | CTGGGCTTAT | CGACTGCACG | GTGCACCAAT | GCTTCTGGCG | TCAGGCAGCC | 60 |
| ATCGGAAGCT | GTGGTATGGC | TGTGCAGGTC | GTAAATCACT | GCATAATTCG | TGTCGCTCAA | 120 |
| GGCGCACTCC | CGTTCTGGAT | AATGTTTTTT | GCGCCGACAT | CATAACGGTT | CTGGCAAATA | 180 |
| TTCTGAAATG | AGCTGTTGAC | AATTAATCAT | CGGCTCGTAT | AATGTGTGGA | ATTGTGAGCG | 240 |
| GATAACAATT | TCACACAGGA | AACAGAATTC | CCGGGGATCC | GTCGACCTGC | AGTCTAGACT | 300 |
| CGAGGGTACC | GCGGCCGCAA | GCTTGGCTGT | TTTGGCGGAT | GAGAGAAGAT | TTTCAGCCTG | 360 |

|  |  |  |  |  | |
|---|---|---|---|---|---|
| ATACAGATTA | AATCAGAACG | CAGAAGCGGT | CTGATAAAAC | AGAATTTGCC | TGGCGGCAGT | 420 |
| AGCGCGGTGG | TCCCACCTGA | CCCCATGCCG | AACTCAGAAG | TGAAACGCCG | TAGCGCCGAT | 480 |
| GGTAGTGTGG | GGTCTCCCCA | TGCGAGAGTA | GGGAACTGCC | AGGCATCAAA | TAAAACGAAA | 540 |
| GGCTCAGTCG | AAAGACTGGG | CCTTTCGTTT | TATCTGTTGT | TTGTCGGTGA | ACGCTCTCCT | 600 |
| GAGTAGGACA | AATCCGCCGG | GAGCGGATTT | GAACGTTGCG | AAGCAACGGC | CCGGAGGGTG | 660 |
| GCGGGCAGGA | CGCCCGCCAT | AAACTGCCAG | GCATCAAATT | AAGCAGAAGG | CCATCCTGAC | 720 |
| GGATGGCCTT | TTTGCGTTTC | TACAAACTCT | TTGTTTATT | TTCTAAATA | CATTCAAATA | 780 |
| TGTATCCGCT | CATGAGACAA | TAACCCTGAT | AAATGCTTCA | ATAATATTGA | AAAAGGAAGA | 840 |
| GTATGAGTAT | TCAACATTTC | CGTGTCGCCC | TTATTCCCTT | TTTTGCGGCA | TTTTGCCTTC | 900 |
| CTGTTTTTGC | TCACCCAGAA | ACGCTGGTGA | AAGTAAAAGA | TGCTGAAGAT | CAGTTGGGTG | 960 |
| CACGAGTGGG | TTACATCGAA | CTGGATCTCA | ACAGCGGTAA | GATCCTTGAG | AGTTTTCGCC | 1020 |
| CCGAAGAACG | TTTTCCAATG | ATGAGCACTT | TTAAAGTTCT | GCTATGTGGC | GCGGTATTAT | 1080 |
| CCCGTAGATC | TGCGCGC |  |  |  |  | 1097 |

(2) INFORMATION FOR SEQ ID NO:8:

(i) SEQUENCE CHARACTERISTICS:
      (A) LENGTH: 3186 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Pseudomonas fluorescens
      (B) STRAIN: CGA267356 (aka MOCG134 and aka BL915)

(vii) IMMEDIATE SOURCE:
      (B) CLONE: pCIB146

(ix) FEATURE:
      (A) NAME/KEY: RBS
      (B) LOCATION: 245..251
      (D) OTHER INFORMATION: /note="potential ribosome binding site"

(ix) FEATURE:
      (A) NAME/KEY: misc_feature
      (B) LOCATION: 256..3006
      (D) OTHER INFORMATION: /product="LemA"
         / note="LemA coding sequence."

(xi) SEQUENCE DESCRIPTION: SEQ ID NO:8:

|  |  |  |  |  | |
|---|---|---|---|---|---|
| GATCCGGGGA | TGGCCGGCAG | ATACGGGATT | CATTGGCTTC | TGCAAGTAAT | TCTCAGTTGC | 60 |
| GCGATTATTC | AAGATTGTCC | GCGGCCGGGC | AACCGACACC | GGTCGACAAA | ACGCTGGCCG | 120 |
| GGCGCCGAGA | CATCCGAGCC | ATTGCGCGGT | CAATTTGCG | AAGAATGCCG | TCAAGCAAAT | 180 |
| GGCTACACTG | CGCAGGTGGT | GCGCACCGGA | CGTGCGCAGG | GTTCATTCAA | AATGGCGTGG | 240 |
| TAGCAGGAGA | GTTGCGTGCT | TAAGAAACTG | GAATCAAAG | GCCGCGTGCT | GTTACTGACC | 300 |
| TTGCTGCCAA | CCAGCCTGAT | GGCGTTGGTA | CTGGGCGGTT | ATTTCACCTG | GATGCAGCAA | 360 |
| TCGGACCTGC | AAACCCAGCT | TCTGCACCGC | GGCGAAATGA | TCGCCGAGCA | ACTGGCGCCC | 420 |
| CTGGTGGCTC | CCGCCCTGGC | CCACCAGGAC | ACTTCCCTGC | TGGAGCGCAT | CGCCACCCAA | 480 |
| TCCCTGGAAC | AGCAGGACGT | GCGCGCAGTG | ACTTTCCTCG | CGCCCGACCG | CACGCCGCTG | 540 |

| | | | | | | |
|---|---|---|---|---|---|---|
| GCCCATGCCG | GCCCGAGCAT | GCTCAACCAG | GCGCCGACCG | GCAACGGCAG | CCAGCTGCTG | 600 |
| CAACGCACCG | GCAGCGACGC | CACCCGCTAT | CTGCTGCCGG | TATTCGGCCG | CCACCGCAAC | 660 |
| CTGGCCGGCG | ACCTGATTCC | CGACGAGTCC | GACCGCCTGC | TCGGCTGGGT | CGAGCTGGAA | 720 |
| CTGTCCCATA | ACAGCATGCT | GCTGCGCGGC | TACCGCAGCC | TGTTCGCCAG | CCTGCTGCTG | 780 |
| ATTACCGCCG | GGCTGATCTG | CACCGGCCTG | CTGGCACTGC | GCATGGGGCG | AACCATCAAC | 840 |
| GACCCGCTGA | GCCAGATCAA | ACAGGCCGTC | ACCCAGCTCA | AGGACGGCAA | CCTGGAAACC | 900 |
| CGCCTGCCCT | TGCTCGGCAG | CCAGGAACTG | GACGAGCTGG | CCTCGGGCAT | CAACCGCATG | 960 |
| GCCGGCACCC | TGCAGAATGC | CCAGGAAGAA | CTGCAGCACA | GCATCGACCA | GGCCACCGAG | 1020 |
| GACGTCCGGC | AAAACCTGGA | GACCATCGAG | ATCCAGAACA | TCGAGCTGGA | CCTGGCGCGC | 1080 |
| AAGGAGGCCC | TGGAGGCCAG | CCGGATCAAG | TCCGAATTCC | TGGCCAACAT | GAGCCATGAA | 1140 |
| ATCCGCACGC | CGCTCAACGG | CATCCTCGGC | TTCACTCATT | TGTTGCAGAA | AAGCGAGCTG | 1200 |
| ACCCCGCGCC | AGCTGGATTA | CCTGGGCACC | ATCGAAAAAT | CCGCCGACAG | CCTGCTGGGA | 1260 |
| ATCATCAACG | AAATTCTCGA | CTTCTCGAAA | ATCGAAGCCG | GCAAGCTGGT | GCTCGACAGC | 1320 |
| ATTCCGTTCA | ACCTGCGCGA | CCTGTTGCAG | GACACCCTGA | CCATTCTCGC | TCCGGCCGCC | 1380 |
| CACGCCAAGC | AGCTGGAACT | GGTCAGCCTG | GTGTATCGCG | ATAGCCCGCT | GTCGCTGGTG | 1440 |
| GGCGACCCGC | TGCGCCTCAA | GCAGATCCTC | ACCAATCTGG | TGAGCAACGC | CATCAAGTTC | 1500 |
| ACCCGCGAAG | GCACCATCGT | CGCCCGGGCC | ATGCTTGAAG | AGGAGCACGA | AGACAGCGTG | 1560 |
| CAACTGCGCA | TCAGCATTCA | GGACACCGGC | ATCGGCCTGT | CGAACCAGGA | CGTGCGCGCC | 1620 |
| CTGTTCCAGG | CGTTCAGCCA | GGCCGACAAT | TCGCTGTCGC | GACAACCCGG | CGGGACTGGC | 1680 |
| CTGGGGCTGG | TGATTTCCAA | GCGCCTGATC | GAACAGATGG | GCGGCGAGAT | CGGCGTCGAC | 1740 |
| AGCACGCCCG | GCGAAGGTTC | GGAGTTCTGG | ATCAGCTGC | GCCTGCCGAA | AACCCGCGAC | 1800 |
| GACGCCGAAG | ACCTGCCGGC | CCCGCCGCTG | CTCGGCAGGC | GGGTCGCGGT | CCTGGAAAAC | 1860 |
| CATGAGCTGG | CGCGCCAGGC | CCTGCAGCAT | CAACTCGAGG | ACTGCGGCCT | GGAAGTCACT | 1920 |
| CCGTTCAACA | CCCTGGAAGC | CCTGACCAAC | GGGGTGACCG | GCGTGCACCA | GACCGACCAG | 1980 |
| GCGATCGATC | TGGCGGTCCT | CGGCATCACC | ACCAACGACA | TGCTGCCGGA | ACGCCTCAAC | 2040 |
| CAGCACATCT | GGGACCTCGA | GCACCTGGGC | TGCAAAGTCC | TGGTGCTGTG | CCCGACCACA | 2100 |
| GAACAGACAC | TCTTCCACCT | GTCGGTGCCC | AACCCTCACA | GCCAGTTGCA | GGCCAAACCG | 2160 |
| GCGTGCACGC | GCAAACTGCG | GCGCGCCCTG | GCCGACCTGG | TCAACCCCAA | GGTGGTGCGC | 2220 |
| AGCGAGCCGA | GCGAACCGAT | CGCCAGCCGC | CGCCACGGG | TGCTGTGTGT | CGATGACAAC | 2280 |
| CCGGCCAACC | TGCTGCTGGT | GCAGACCCTG | CTCGAAGACA | TGGGCGCCAA | AGTGCTCGCG | 2340 |
| GTCGACAGCG | GCTATGCGGC | GGTCAAGGCG | GTGCAGAGCG | AGTCGTTCGA | CCTGGTGATG | 2400 |
| ATGGACGTGC | AGATGCCCGG | CATGGACGGT | CGCCAGAGCA | CCGAGGCGAT | TCGCCAGTGG | 2460 |
| GAAAGCGGGC | GCAACTGCTC | GCCGCTGCCG | GTGATCGCCC | TCACCGCCCA | CGCCATGGCC | 2520 |
| AACGAAAAAC | GCGCGCTGCT | GCAAAGCGGC | ATGGACGATT | ACCTGACCAA | ACCCATCAGT | 2580 |
| GAGCGGCAAC | TGGCCCAGGT | GGTGCTGAAG | TGGACCGGCC | TGGCCCTGCG | CAACCAAGGT | 2640 |
| CCGGAACGCT | CTGGCGAAGT | GTCTGGCAAC | GGCCTCGAGC | TGCAAGTGCT | GGATCACGAC | 2700 |
| GAAGGCTTGC | TCCTGGCCGC | CGGCAAGGCG | GACCTGGCGG | CCGACATGCT | GGCCATGCTC | 2760 |
| CTGGCCTCGC | TGGAAGCCGA | TCGCGAAGCG | ATTCGCGCCG | CCCGTGCCGC | CAACGATCAC | 2820 |
| AATGCGTTGA | TCGAGCGGGT | CCATCGCCTG | CACGGGCGA | CCCGCTATTG | TGGCGTGCCG | 2880 |
| CAGTTGCGCG | CCGCCTGCCA | GCGCAGCGAA | ACCCTGCTCA | AGCAGGAAGA | CGTCAAGGCC | 2940 |

```
TTCGCCGCCC TCGACGAGCT CGAACGGGCC ATTAGTCGCC TGGCCACGGA GGCCCGCATC    3000

AACGCCTGAT TCAAGGCAAC GACACGTCAG CCCCGCAGGT TCATGCTCGG GGCAACTTTC    3060

ACAAGGACGA CGCCATGCGC ACGATTCTCT TCAGCAGCCA GAACTATGAC CGCGACAGCT    3120

TCCTCGGCGC CGCCCTGCCG CCGGGCATCG AGCTGCAATT CCAGGCGGCG CGCCTGAGCC    3180

TGGACA                                                              3186
```

( 2 ) INFORMATION FOR SEQ ID NO:9:

( i ) SEQUENCE CHARACTERISTICS:
        ( A ) LENGTH: 642 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: CGA375260

( i x ) FEATURE:
        ( A ) NAME/KEY: CDS
        ( B ) LOCATION: 1..639
        ( D ) OTHER INFORMATION: /product="gac*A gene"
        ( D ) OTHER INFORMATION: /transl_except=(pos: 1 .. 3, aa: Met ( x i ) SEQUENCE DESCRIPTION: SEQ ID NO:9:

```
TTG ATT AGG GTG CTA GTA GTC GAT GAC CAT GAT CTC GTT CGT ACA GGT       48
Met Ile Arg Val Leu Val Val Asp Asp His Asp Leu Val Arg Thr Gly
 1               5                  10                  15

ATT ACA CGA ATG CTG GCT GAC ATC GAT GGC CTG CAA GTG GTC GGC CAG       96
Ile Thr Arg Met Leu Ala Asp Ile Asp Gly Leu Gln Val Val Gly Gln
            20                  25                  30

GCC GAG TCA GGG GAG GAA TCC CTG CTC AAG GCC CGG GAG TTG AAA CCC      144
Ala Glu Ser Gly Glu Glu Ser Leu Leu Lys Ala Arg Glu Leu Lys Pro
        35                  40                  45

GAT GTG GTC CTC ATG GAC GTC AAG ATG CCC GGG ATC GGC GGT CTT GAA      192
Asp Val Val Leu Met Asp Val Lys Met Pro Gly Ile Gly Gly Leu Glu
    50                  55                  60

GCC ACG CGC AAA TTG TTG CGC AGT CAC CCG GAT ATC AAA GTC GTG GCC      240
Ala Thr Arg Lys Leu Leu Arg Ser His Pro Asp Ile Lys Val Val Ala
65                  70                  75                  80

GTC ACC GTG TGT GAA GAA GAT CCG TTC CCG ACC CGC TTG CTG CAA GCC      288
Val Thr Val Cys Glu Glu Asp Pro Phe Pro Thr Arg Leu Leu Gln Ala
                85                  90                  95

GGC GCG GCG GGT TAC CTG ACC AAG GGG GCG GGC CTC AAT GAA ATG GTG      336
Gly Ala Ala Gly Tyr Leu Thr Lys Gly Ala Gly Leu Asn Glu Met Val
            100                 105                 110

CAG GCC ATT CGC CTG GTG TTT GCC GGC CAG CGT TAC ATC AGC CCG CAA      384
Gln Ala Ile Arg Leu Val Phe Ala Gly Gln Arg Tyr Ile Ser Pro Gln
        115                 120                 125

ATT GCC CAG CGG TTG GTG TTC AAG TCA TTC CAG CCT TCC AGT GAT TCA      432
Ile Ala Gln Arg Leu Val Phe Lys Ser Phe Gln Pro Ser Ser Asp Ser
    130                 135                 140

CCG TTC GAT GCT TTG TCC GAG CGG GAA ATC CAG ATC GCG CTG ATG ATT      480
Pro Phe Asp Ala Leu Ser Glu Arg Glu Ile Gln Ile Ala Leu Met Ile
145                 150                 155                 160

GTC GGC TGC CAG AAA GTG CAG ATC ATC TCC GAC AAG CTG TGC CTG TCT      528
Val Gly Cys Gln Lys Val Gln Ile Ile Ser Asp Lys Leu Cys Leu Ser
                165                 170                 175
```

| | | | | | | | | | | | | | | | |
|---|---|---|---|---|---|---|---|---|---|---|---|---|---|---|---|
| CCG | AAA | ACC | GTT | AAT | ACC | TAC | CGT | TAC | CGC | ATC | TTC | GAA | AAG | CTC | TCG | 576 |
| Pro | Lys | Thr | Val | Asn | Thr | Tyr | Arg | Tyr | Arg | Ile | Phe | Glu | Lys | Leu | Ser |
| | | | 180 | | | | 185 | | | | | | 190 | | |
| ATC | AGC | AGC | GAT | GTT | GAA | CTG | ACA | TTG | CTG | GCG | GTT | CGC | CAC | GGC | ATG | 624 |
| Ile | Ser | Ser | Asp | Val | Glu | Leu | Thr | Leu | Leu | Ala | Val | Arg | His | Gly | Met |
| | | 195 | | | | 200 | | | | | | 205 | | | |
| GTC | GAT | GCC | AGT | GCC | TGA | | | | | | | | | | | 642 |
| Val | Asp | Ala | Ser | Ala | | | | | | | | | | | |
| | | 210 | | | | | | | | | | | | | |

( 2 ) INFORMATION FOR SEQ ID NO:10:

( i ) SEQUENCE CHARACTERISTICS:
( A ) LENGTH: 213 amino acids
( B ) TYPE: amino acid
( D ) TOPOLOGY: linear ( i i ) MOLECULE TYPE: protein ( x i ) SEQUENCE DESCRIPTION: SEQ ID NO:10:

| Met | Ile | Arg | Val | Leu | Val | Val | Asp | Asp | His | Asp | Leu | Val | Arg | Thr | Gly |
|---|---|---|---|---|---|---|---|---|---|---|---|---|---|---|---|
| 1 | | | | 5 | | | | | 10 | | | | | 15 | |

| Ile | Thr | Arg | Met | Leu | Ala | Asp | Ile | Asp | Gly | Leu | Gln | Val | Val | Gly | Gln |
|---|---|---|---|---|---|---|---|---|---|---|---|---|---|---|---|
| | | | 20 | | | | 25 | | | | | 30 | | | |

| Ala | Glu | Ser | Gly | Glu | Glu | Ser | Leu | Leu | Lys | Ala | Arg | Glu | Leu | Lys | Pro |
|---|---|---|---|---|---|---|---|---|---|---|---|---|---|---|---|
| | | 35 | | | | 40 | | | | | 45 | | | | |

| Asp | Val | Val | Leu | Met | Asp | Val | Lys | Met | Pro | Gly | Ile | Gly | Gly | Leu | Glu |
|---|---|---|---|---|---|---|---|---|---|---|---|---|---|---|---|
| | 50 | | | | 55 | | | | | 60 | | | | | |

| Ala | Thr | Arg | Lys | Leu | Leu | Arg | Ser | His | Pro | Asp | Ile | Lys | Val | Val | Ala |
|---|---|---|---|---|---|---|---|---|---|---|---|---|---|---|---|
| 65 | | | | | 70 | | | | 75 | | | | | | 80 |

| Val | Thr | Val | Cys | Glu | Glu | Asp | Pro | Phe | Pro | Thr | Arg | Leu | Leu | Gln | Ala |
|---|---|---|---|---|---|---|---|---|---|---|---|---|---|---|---|
| | | | | 85 | | | | | 90 | | | | | 95 | |

| Gly | Ala | Ala | Gly | Tyr | Leu | Thr | Lys | Gly | Ala | Gly | Leu | Asn | Glu | Met | Val |
|---|---|---|---|---|---|---|---|---|---|---|---|---|---|---|---|
| | | | 100 | | | | 105 | | | | | 110 | | | |

| Gln | Ala | Ile | Arg | Leu | Val | Phe | Ala | Gly | Gln | Arg | Tyr | Ile | Ser | Pro | Gln |
|---|---|---|---|---|---|---|---|---|---|---|---|---|---|---|---|
| | | 115 | | | | 120 | | | | | 125 | | | | |

| Ile | Ala | Gln | Arg | Leu | Val | Phe | Lys | Ser | Phe | Gln | Pro | Ser | Ser | Asp | Ser |
|---|---|---|---|---|---|---|---|---|---|---|---|---|---|---|---|
| | 130 | | | | 135 | | | | | 140 | | | | | |

| Pro | Phe | Asp | Ala | Leu | Ser | Glu | Arg | Glu | Ile | Gln | Ile | Ala | Leu | Met | Ile |
|---|---|---|---|---|---|---|---|---|---|---|---|---|---|---|---|
| 145 | | | | | 150 | | | | 155 | | | | | | 160 |

| Val | Gly | Cys | Gln | Lys | Val | Gln | Ile | Ile | Ser | Asp | Lys | Leu | Cys | Leu | Ser |
|---|---|---|---|---|---|---|---|---|---|---|---|---|---|---|---|
| | | | | 165 | | | | | 170 | | | | | 175 | |

| Pro | Lys | Thr | Val | Asn | Thr | Tyr | Arg | Tyr | Arg | Ile | Phe | Glu | Lys | Leu | Ser |
|---|---|---|---|---|---|---|---|---|---|---|---|---|---|---|---|
| | | | 180 | | | | 185 | | | | | | 190 | | |

| Ile | Ser | Ser | Asp | Val | Glu | Leu | Thr | Leu | Leu | Ala | Val | Arg | His | Gly | Met |
|---|---|---|---|---|---|---|---|---|---|---|---|---|---|---|---|
| | | 195 | | | | 200 | | | | | | 205 | | | |

| Val | Asp | Ala | Ser | Ala |
|---|---|---|---|---|
| | | 210 | | |

( 2 ) INFORMATION FOR SEQ ID NO:11:

( i ) SEQUENCE CHARACTERISTICS:
( A ) LENGTH: 5698 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
(A) ORGANISM: Pseudomonas aureofaciens
(B) STRAIN: 30-84

(vii) IMMEDIATE SOURCE:
(B) CLONE: phzFABCD (ix) FEATURE:
(A) NAME/KEY: misc_feature
(B) LOCATION: 105..1307
(D) OTHER INFORMATION: /product="phzF"
/ note="ORF1"

(ix) FEATURE:
(A) NAME/KEY: misc_feature
(B) LOCATION: 1323..1946
(D) OTHER INFORMATION: /product="phzA"
/ note="ORF2"

(ix) FEATURE:
(A) NAME/KEY: misc_feature
(B) LOCATION: 1943..3856
(D) OTHER INFORMATION: /product="phzB"
/ note="ORF3"

(ix) FEATURE:
(A) NAME/KEY: misc_feature
(B) LOCATION: 3859..4695
(D) OTHER INFORMATION: /product="phzC"
/ note="ORF4"

(ix) FEATURE:
(A) NAME/KEY: misc_feature
(B) LOCATION: 4692..5360
(D) OTHER INFORMATION: /product="phzD"
/ note="ORF5"

(xi) SEQUENCE DESCRIPTION: SEQ ID NO:11:

```
GAATTCATGA ACGTCTTTCA GCAACTGCGC GCCCTGGGTA TTCCAGTACC GCAAATCAAG    60
CGCGAAGGCA TTCCAACTTA ATCCCTCGTG AGAGTGATCG CATCATGGAA GACTTACTGA   120
AACGGGTTTT AAGTTGTGAA GCGTTCCAGC AGCCTCAATG GAGCGAGCCC TCACAATTGC   180
ATGACGCGCA GGCCTACCTC AGGGACAGCG CCTCATTGAT ACGAGTGGAA GACATCCTGG   240
TGCTGCGCGC CACGCTGGCG CGTGTAGCGG CCGGCGAAGC AATGGTCATC CAGTCCGGTG   300
ACTGCGCCGA GGACATGGAT GAAAGCACTC CCGACCATGT GGCCCGCAAA GCCGCGGTAC   360
TGGACATCCT GGCCGGTACG TTCCGGCTGG TGACCCAACA ACCGGTGGTA CGGGTGGGAC   420
GAATTGCCGG GCAGTTTGCC AAGCCGCGTT CCAACAACAA CGAACGCATC GGCGATGTCG   480
AATTACCGGT GTATCGCGGC GACATGGTCA ACGGTCGCGA GGCCGTCTGC GGTCATCGCC   540
AGCACGATGC GCAACGCCTG GTTCGAGGCT ATAGCGCCGC GCGGGACATC ATGCAACACC   600
TGGGCTGGAA AGCCTCGGCA AGCCAGGAAC AACTCAGCGG TTCACCGGCC TGGACCAACC   660
ATGAAATGCT GGTACTCGAC TACGAACTGC CACAACTGCG CCAGGACGAA CAGGGCCGGG   720
TATTTCTCGG TTCTACCCAC TGGCCGTGGA TCGGCGAGCG TACCCGTCAG TTAACGGGCG   780
CTCACGTGAC GCTGCTCAGC GAAGTGCTCA ATCCGGTGGC GTGCAAGGTC GGCCCGGACA   840
TTACCCAAGA CCAGTTACTG AGCCTGTGTG AACGCCTGGA CGCCAAGCGC GAACCCGGCC   900
GGCTGACCCT GATTGCCCGC ATGGGCGCGC AAAAGGTCGC CGAGCGCCTG CCGCCGCTGG   960
TCGAAGCGGT GCGCCAGGCC GGCCACAAGA TCATCTGGCT GAGCGACCCG ATGCACGGCA  1020
ACACCATCGT CGCGCCCTGC GGCAACAAGA CCCGCATGGT GCAGGCCATC ACCGAGGAAA  1080
TCGCCGCCTT CAAGCATGCC GTGACCTCCG CCGGTGGCGT GGCCGCCGGC CTGCACCTGG  1140
AAACCACCCC TGACGACGTC AGCGAGTGCG CTTCCGATGC CGCCGGCCTG CATCAGGTCG  1200
```

| | | | | | |
|---|---|---|---|---|---|
| CCAGCCGCTA | CAAAAGCCTG | TGCGACCCGC | GCCTGAACCC | CTGGCAAGCC | ATTACTGCGG | 1260 |
| TGATGGCCTG | GAAAAACCAG | CCCTCTTCAA | CCCTTGCCTC | CTTTTGACTG | GAGTTTGTCG | 1320 |
| TCATGACCGG | CATTCCATCG | ATCGTCCCTT | ACGCCTTGCC | TACCAACCGC | GACCTGCCCG | 1380 |
| TCAACCTCGC | GCAATGGAGC | ATCGACCCCG | AGCGTGCCGT | GCTGCTGGTG | CATGACATGC | 1440 |
| AGCGCTACTT | CCTGCGGCCC | TTGCCCGACG | CCCTGCGTGA | CGAAGTCGTG | AGCAATGCCG | 1500 |
| CGCGCATTCG | CCAGTGGGCT | GCCGACAACG | GCGTTCCGGT | GGCCTACACC | GCCCAGCCCG | 1560 |
| GCAGCATGAG | CGAGGAGCAA | CGCGGGCTGC | TCAAGGACTT | CTGGGGCCCG | GGCATGAAGG | 1620 |
| CCAGCCCCGC | CGACCGCGAG | GTGGTCGGCG | CCCTGACGCC | CAAGCCCGGC | GACTGGCTGC | 1680 |
| TGACCAAGTG | GCGCTACAGC | GCGTTCTTCA | ACTCCGACCT | GCTGGAACGC | ATGCGCGCCA | 1740 |
| ACGGGCGCGA | TCAGTTGATC | CTGTGCGGGG | TGTACGCCCA | TGTCGGGGTA | CTGATTTCCA | 1800 |
| CCGTGGATGC | CTACTCCAAC | GATATCCAGC | CGTTCCTCGT | TGCCGACGCG | ATCGCCGACT | 1860 |
| TCAGCAAAGA | GCACCACTGG | ATGGCCATCG | AATACGCCGC | CAGCCGTTGC | GCCATGGTCA | 1920 |
| TCACCACCGA | CGAGGTGGTG | CTATGAGCCA | GACCGCAGCC | CACCTCATGG | AACGCATCCT | 1980 |
| GCAACCGGCT | CCCGAGCCGT | TTGCCCTGTT | GTACCGCCCG | GAATCCAGTG | GCCCCGGCCT | 2040 |
| GCTGGACGTG | CTGATCGGCG | AAATGTCGGA | ACCGCAGGTC | CTGGCCGATA | TCGACTTGCC | 2100 |
| TGCCACCTCG | ATCGGCGCGC | CTCGCCTGGA | TGTACTGGCG | CTGATCCCCT | ACCGCCAGAT | 2160 |
| CGCCGAACGC | GGTTTCGAGG | CGGTGGACGA | TGAGTCGCCG | CTGCTGGCGA | TGAACATCAC | 2220 |
| CGAGCAGCAA | TCCATCAGCA | TCGAGCGCTT | GCTGGGAATG | CTGCCCAACG | TGCCGATCCA | 2280 |
| GTTGAACAGC | GAACGCTTCG | ACCTCAGCGA | CGCGAGCTAC | GCCGAGATCG | TCAGCCAGGT | 2340 |
| GATCGCCAAT | GAAATCGGCT | CCGGGGAAGG | CGCCAACTTC | GTCATCAAAC | GCACCTTCCT | 2400 |
| GGCCGAGATC | AGCGAATACG | GCCCGGCCAG | TGCGCTGTCG | TTCTTTCGCC | ATCTGCTGGA | 2460 |
| ACGGGAGAAA | GGCGCCTACT | GGACGTTCAT | CATCCACACC | GGCAGCCGTA | CCTTCGTGGG | 2520 |
| TGCGTCCCCC | GAGCGCCACA | TCAGCATCAA | GGATGGGCTC | TCGGTGATGA | CCCCATCAG | 2580 |
| CGGCACTTAC | CGCTATCCGC | CCGCCGGCCC | CAACCTGTCG | GAAGTCATGG | ACTTCCTGGC | 2640 |
| GGATCGCAAG | GAAGCCGACG | AGCTCTACAT | GGTGGTGGAT | GAAGAGCTGA | AAATGATGGC | 2700 |
| GCGCATTTGT | GAGGACGGCG | CCACGTCCT | CGGCCCTTAC | CTCAAGGAAA | TGGCGCACCT | 2760 |
| GGCCCACACC | GAGTACTTCA | TCGAAGGCAA | GACCCATCGC | GATGTACGGG | AAATCCTGCG | 2820 |
| CGAAACCCTG | TTTGCGCCCA | CCGTCACCGG | CAGCCCACTG | GAAAGCGCCT | GCCGGGTCAT | 2880 |
| CCAGCGCTAT | GAGCCGCAAG | GCCGCGCGTA | CTACAGCGGC | ATGGCTGCGC | TGATCGGCAG | 2940 |
| CGATGGCAAG | GGCGGGCGTT | CCCTGGACTC | CGCGATCCTG | ATTCGTACCG | CCGACATCGA | 3000 |
| TAACAGCGGC | GAGGTGCGGA | TCAGCGTGGG | CTCGACCATC | GTGCCGCATT | CCGACCCGAT | 3060 |
| GACCGAGGCT | GCCGAAAGCC | GGGCCAAGGC | CACTGGCCTG | ATCAGCGCAC | TGAAAAACCA | 3120 |
| GGCGCCCTCG | CGCTTCGGCA | ATCACCTGCA | AGTGCGCGCC | GCATTGGCCA | GCCGCAATGC | 3180 |
| CTACGTCTCG | GACTTCTGGC | TGATGGACAG | CCAGCAGCGG | GAGCAGATCC | AGGCCGACTT | 3240 |
| CAGTGGGCGC | CAGGTGCTGA | TCGTCGACGC | CGAAGACACC | TTCACCTCGA | TGATCGCCAA | 3300 |
| GCAACTGCGG | GCCCTGGGCC | TGGTAGTGAC | GGTGTGCAGC | TTCAGCGACG | AATACAGCTT | 3360 |
| TGAAGGCTAC | GACCTGGTCA | TCATGGGCCC | CGGCCCCGGC | AACCCGAGCG | AAGTCCAACA | 3420 |
| GCCGAAAATC | AACCACCTGC | ACGTGGCCAT | CCGCTCCTTG | CTCAGCCAGC | AGCGGCCATT | 3480 |
| CCTCGCGGTG | TGCCTGAGCC | ATCAGGTGCT | GAGCCTGTGC | CTGGGCCTGG | AACTGCAGCG | 3540 |
| CAAAGCCATT | CCCAACCAGG | GCGTGCAAAA | ACAGATCGAC | CTGTTTGGCA | ATGTCGAACG | 3600 |

-continued

| | | | | | |
|---|---|---|---|---|---|
| GGTGGGTTTC | TACAACACCT | TCGCCGCCCA | GAGCTCGAGT | GACCGCCTGG | ACATCGACGG | 3660
| CATCGGCACC | GTCGAAATCA | GCCGCGACAG | CGAGACCGGC | GAGGTGCATG | CCCTGCGTGG | 3720
| CCCCTCGTTC | GCCTCCATGC | AGTTTCATGC | CGAGTCGCTG | CTGACCCAGG | AAGGTCCGCG | 3780
| CATCATCGCC | GACCTGCTGC | GGCACGCCCT | GATCCACACA | CCTGTCGAGA | ACAACGCTTC | 3840
| GGCCGCCGGG | AGATAACCAT | GGAGCATTAC | GTCATCATCG | ACGCCTTTGC | CAGCGTCCCG | 3900
| CTGGAAGGCA | ATCCGGTCGC | GGTGTTCTTT | GACGCCGATG | ACTTGTCGGC | CGAGCAAATG | 3960
| CAACGCATTG | CCCGGGAGAT | GAACCTGTCG | GAAACCACTT | TCGTGCTCAA | GCCACGTAAC | 4020
| TGCGGCGATG | CGCTGATCCG | GATCTTCACC | CCGGTCAACG | AACTGCCCTT | CGCCGGGCAC | 4080
| CCGTTGCTGG | GCACGGACAT | TGCCCTGGGT | GCGCGCACCG | ACAATCACCG | GCTGTTCCTG | 4140
| GAAACCCAGA | TGGGCACCAT | CGCCTTTGAG | CTGGAGCGCC | AGAACGGCAG | CGTCATCGCC | 4200
| GCCAGCATGG | ACCAGCCGAT | ACCGACCTGG | ACGGCCCTGG | GGCGCGACGC | CGAGTTGCTC | 4260
| AAGGCCCTGG | GCATCAGCGA | CTCGACCTTT | CCCATCGAGA | TCTATACAA | CGGCCCGCGT | 4320
| CATGTGTTTG | TCGGCCTGCC | AAGCATCGCC | GCGCTGTCGG | CCCTGCACCC | CGACCACCGT | 4380
| GCCCTGTACA | GCTTCCACGA | CATGGCCATC | AACTGTTTTG | CCGGTGCGGG | ACGGCGCTGG | 4440
| CGCAGCCGGA | TGTTCTCGCC | GGCCTATGGG | GTGGTCGAGG | ATGCGGCCAC | GGGCTCCGCT | 4500
| GCCGGGCCCT | TGGCGATCCA | TCTGGCGCGG | CATGGCCAGA | TCGAGTTCGG | CCAGCAGATC | 4560
| GAAATTCTTC | AGGGCGTGGA | AATCGGCCGC | CCCTCACTCA | TGTTCGCCCG | GGCCGAGGGC | 4620
| CGCGCCGATC | AACTGACGCG | GGTCGAAGTA | TCAGGCAATG | GCATCACCTT | CGGACGGGGG | 4680
| ACCATCGTTC | TATGAACAGT | TCAGTACTAG | GCAAGCCGCT | GTTGGGTAAA | GGCATGTCGG | 4740
| AATCGCTGAC | CGGCACACTG | GATGCGCCGT | TCCCCGAGTA | CCAGAAGCCG | CCTGCCGATC | 4800
| CCATGAGCGT | GCTGCACAAC | TGGCTCGAAC | GCGCACGCCG | CGTGGGCATC | CGCGAACCCC | 4860
| GTGCGCTGGC | GCTGGCCACG | GCTGACAGCC | AGGGCCGGCC | TTCGACACGC | ATCGTGGTGA | 4920
| TCAGTGAGAT | CAGTGACACC | GGGGTGCTGT | TCAGCACCCA | TGCCGGAAGC | CAGAAAGGCC | 4980
| GCGAACTGAC | AGAGAACCCC | TGGGCCTCGG | GGACGCTGTA | TTGGCGCGAA | ACCAGCCAGC | 5040
| AGATCATCCT | CAATGGCCAG | GCCGTGCGCA | TGCCGGATGC | CAAGGCTGAC | GAGGCCTGGT | 5100
| TGAAGCGCCC | TTATGCCACG | CATCCGATGT | CATCGGTGTC | TCGCCAGAGT | GAAGAACTCA | 5160
| AGGATGTTCA | AGCCATGCGC | AACGCCGCCA | GGGAACTGGC | CGAGGTTCAA | GGTCCGCTGC | 5220
| CGCGTCCCGA | GGGTTATTGC | GTGTTTGAGT | TACGGCTTGA | ATCGCTGGAG | TTCTGGGGTA | 5280
| ACGGCGAGGA | GCGCCTGCAT | GAACGCTTGC | GCTATGACCG | CAGCGCTGAA | GGCTGGAAAC | 5340
| ATCGCCGGTT | ACAGCCATAG | GGTCCCGCGA | TAAACATGCT | TTGAAGTGCC | TGGCTGCTCC | 5400
| AGCTTCGAAC | TCATTGCGCA | AACTTCAACA | CTTATGACAC | CCGGTCAACA | TGAGAAAAGT | 5460
| CCAGATGCGA | AAGAACGCGT | ATTCGAAATA | CCAAACAGAG | AGTCCGGATC | ACCAAAGTGT | 5520
| GTAACGACAT | TAACTCCTAT | CTGAATTTTA | TAGTTGCTCT | AGAACGTTGT | CCTTGACCCA | 5580
| GCGATAGACA | TCGGGCCAGA | ACCTACATAA | ACAAAGTCAG | ACATTACTGA | GGCTGCTACC | 5640
| ATGCTAGATT | TTCAAAACAA | GCGTAAATAT | CTGAAAAGTG | CAGAATCCTT | CAAAGCTT | 5698

What is claimed is:

1. A biocontrol strain of *Pseudomonas fluorescens* selected from the following group consisting of: CGA376146 (NRRL B-21811), CGA364473 (NRRL B-21812), CGA375258 (NRRL B-21813), CGA376148 (NRRL B-21814), CGA364476 (NRRL B-21815), CGA375260 (NRRL B-21816), CGA375259 (NRRL B-21817), CGA378584 (NRRL B-21818), and CGA267pPhz (NRRL B-21819).

2. A biocontrol strain of *Pseudomonas fluorescens* according to claim 1, which is CGA376146 (NRRL B-21811).

3. A biocontrol strain of *Pseudomonas fluorescens* according to claim 1, which is CGA364473 (NRRL B-21812).

4. A biocontrol strain of *Pseudomonas fluorescens* according to claim 1, which is CGA375258 (NRRL B-21813).

5. A biocontrol strain of *Pseudomonas fluorescens* according to claim 1, which is CGA376148 (NRRL B-21814).

6. A biocontrol strain of *Pseudomonas fluorescens* according to claim 1, which is CGA364476 (NRRL B-21815).

7. A biocontrol strain of *Pseudomonas fluorescens* according to claim 1, which is CGA375260 (NRRL B-21816).

8. A biocontrol strain of *Pseudomonas fluorescens* according to claim 1, which is CGA375259 (NRRL B-21817).

9. A biocontrol strain of *Pseudomonas fluorescens* according to claim 1, which is CGA378584 (NRRL B-21818).

10. A biocontrol strain of *Pseudomonas fluorescens* according to claim 1, which is CGA267pPhz (NRRL B-21819).

11. A method for controlling or inhibiting the growth of a plant pathogenic fungus by applying an effective amount of the biocontrol strain of claim 1 to an environment in which the plant pathogenic fungus may grow.

12. A method for controlling or inhibiting the growth of a plant pathogenic fungus by applying an effective amount of the biocontrol strain of claim 1 to a plant or plant part in order to protect said plant or plant part from a plant pathogenic fungus.

13. A method for controlling or inhibiting the growth of a plant pathogenic fungus by applying an effective amount of the biocontrol strain of claim 1 to seed in order to protect a plant that develops from said seed from a plant pathogenic fungus.

14. The method of claim 11, wherein said plant pathogenic fungus is Rhizoctonia or Pythium.

15. The method of claim 13, wherein said plant pathogenic fungus is Rhizoctonia or Pythium.

16. The method of claim 13, wherein said plant pathogenic fungus is Rhizoctonia or Pythium.

17. A biocontrol composition comprising the biocontrol strain of claim 1 in combination with a chemical fungicide.

18. The biocontrol composition of claim 17, wherein said chemical fungicide is a metalaxyl compound.

19. A method for controlling or inhibiting the growth of a plant pathogenic fungus by applying an effective amount of the biocontrol composition of claim 17 to an environment in which the plant pathogenic fungus may grow.

20. A method for controlling or inhibiting the growth of a plant pathogenic fungus by applying an effective amount of the biocontrol composition of claim 17 to a plant or plant part in order to protect said plant or plant part from a plant pathogenic fungus.

21. A method for controlling or inhibiting the growth of a plant pathogenic fungus by applying an effective amount of the biocontrol composition of claim 17 to seed in order to protect a plant that develops from said seed from a plant pathogenic fungus.

* * * * *